United States Patent
Pazenok et al.

(10) Patent No.: US 10,266,494 B2
(45) Date of Patent: Apr. 23, 2019

(54) PROCESS FOR THE PREPARATION OF POLYFLUOROALKYLATED QUINOLINES

(71) Applicants: Bayer CropScience Aktiengesellschaft, Monheim am Rhein (DE); CENTRE NATIONAL DE LA RECHERCHE SCIENTIFIQUE, Paris (FR)

(72) Inventors: Sergii Pazenok, Solingen (DE); Jean-Pierre Vors, Sainte Foy les Lyon (FR); Frédéric R Leroux, Herrlisheim (FR); Fallia Aribi, Beauvais (FR); Etienne Schmitt, Strasbourg (FR); Armen Panossian, Strasbourg (FR)

(73) Assignees: Bayer CropScience Aktiengesellschaft, Monheim am Rhein (DE); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/070,561

(22) PCT Filed: Jan. 13, 2017

(86) PCT No.: PCT/EP2017/050642
§ 371 (c)(1),
(2) Date: Jul. 17, 2018

(87) PCT Pub. No.: WO2017/125318
PCT Pub. Date: Jul. 27, 2017

(65) Prior Publication Data
US 2019/0023659 A1    Jan. 24, 2019

(30) Foreign Application Priority Data

Jan. 21, 2016  (EP) .................... 16290017

(51) Int. Cl.
| | | |
|---|---|---|
| *C07D 215/18* | (2006.01) |
| *C07D 215/12* | (2006.01) |
| *C07D 215/26* | (2006.01) |
| *C07D 215/36* | (2006.01) |
| *C07D 215/38* | (2006.01) |

(52) U.S. Cl.
CPC ......... *C07D 215/18* (2013.01); *C07D 215/12* (2013.01); *C07D 215/26* (2013.01); *C07D 215/36* (2013.01); *C07D 215/38* (2013.01)

(58) Field of Classification Search
CPC .. C07D 215/18; C07D 215/12; C07D 215/26; C07D 215/36; C07D 215/38
See application file for complete search history.

(56) References Cited

FOREIGN PATENT DOCUMENTS

WO       2014187773 A1       11/2014

OTHER PUBLICATIONS

L. Strekowski, et al., "Synthesis of 4-Perflouroalkylquinolines," Tetrahedron, vol. 54, No. 28, Jul. 9, 1998, pp. 7947-7954, pp. 7948-7950 (schemes 1-3), XP002755964.
J.C. Sloop, "Quinoline formation via a modified Combes reaction: examination of kinetics, substituent effects, and mechanistic pathways," Journal of Physical Organic Chemistry, vol. 22, Aug. 26, 2008, pp. 110-117, Reaction schemes 1-3, XP002755965.
J.C. Sloop et al., "Syntheis of fluorinated heterocycles," Journal of Fluorine Chemistry, vol. 118, Oct. 1, 2002, pp. 135-147, Reaction scheme 6, Table 3, XP002755966.
L. Strekowski, et al., "Amination by Lithium Alkylamide Reagents of Ketimines Derived from 2-(Trifluoromethyl) anilines and Methyl Halophenyl Ketones and Their Cyclization Products 2-(Halophenyl)quinolin-4-amines," Tetrahedron, vol. 52, No. 9, May 15, 1996, pp. 3273-3282, Reaction schemes 1-3, XP002755967.
F. Zhao et al., "The reaction of 2-fluoroalkyl-1-iodoethylenes with arylamines: a facile method for the synthesis of fluoroalkylated quinolines and enaminoketones," Tetrahedron, vol. 60, No. 44, Oct. 25, 2004, pp. 9945-9951, Tables 1-4, XP004580195.
European Search Report of European Patent Application No. EP 16290017 dated Mar. 31, 2016.
International Search Report of International Patent Application No. PCT/EP2017/050642 dated Feb. 22, 2017.

*Primary Examiner* — Timothy R Rozof
(74) *Attorney, Agent, or Firm* — McBee Moore Woodward & Vanik IP, LLC

(57) ABSTRACT

The invention relates to a novel process for preparing polyfluoroalkylated quinolines from ketimines in the presence of fluoroalkylamino reagents.

5 Claims, No Drawings

PROCESS FOR THE PREPARATION OF POLYFLUOROALKYLATED QUINOLINES

CROSS REFERENCE TO RELATED APPLICATIONS

This application is a National Stage entry of International Application No. PCT/EP2017/050642 filed 13 Jan. 2017, which claims priority to European Patent Application No. 16290017.9, filed 21 Jan. 2016.

BACKGROUND

Field

The invention relates to a novel process for preparing polyfluoroalkylated quinolines from ketimines in the presence of fluoroalkylamino reagents.

Description of Related Art

Quinolines are important precursors to pharmaceuticals and agrochemicals ((a) J. Sloop, *J. Phys. Org. Chem.*, 2009, 22, 110-117; (b) A. R. Surrey and H. F. Hammer, *J. Am. Chem. Soc.*, 1946, 68, 113-116; (c) W. Jonhson and B. G. Buetl, *J. Am. Chem. Soc.*, 1952, 74, 4513-4516; (d) J. Mulero, G. Martinez, J. Oliva, S. Cermeno, J. M. Cayuela, P. Zafrilla, A. Martinez-Cacha and A. Barba, *Food Chem,* 2015, 180, 25-31).

The Combes reaction starting from β-diketones and anilines is an important method for the synthesis of quinolines (*Chem. Ber.,* 1896, 29, 2456). However the Combes reaction has only limited importance for the preparation of quinolines containing perfluoroalkyl groups in position 2 and 4. J. Sloop et al. (*J. Fluorine Chem.,* 2002, 118, 135-147) described an application of the Combes synthesis using anilines and fluorinated β-diketones in polyphosphoric acid. The fluorinated β-diketones usually prepared via Claisen condensation are hardly accessible. Especially in the case of fluorinated β-diketones the yields of this reaction are rather low and the isolation of the highly volatile products is quite difficult. Moreover, a cyclization of unsymmetrical β-diketones under Combes conditions leads to the formation of regioisomers (see J. Sloop et al., *J. Fluorine Chem.,* 2002, 118, 135-147). In addition, the isolation of quinolines from the reaction mixture containing polyphosphoric acid produces large amount of P-containing waste.

SUMMARY

In the light of the prior art described above, it is an object of the present invention to provide an efficient, regioselective process using cheap starting materials yielding fluorinated quinolines derivatives.

The object described above was achieved by a process for preparing quinoline derivatives of the formula (I)

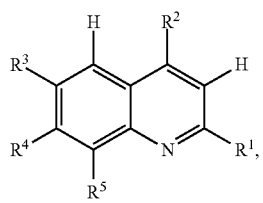

in which
$R^1$ is $C_{1-5}$-haloalkyl, aryl,
$R^2$ is $C_{1-5}$-haloalkyl, $C_{2-6}$-haloalkylhaloalkoxy
and $R^3$, $R^4$, $R^5$ are each independently selected from H, $C_{1-5}$-alkyl, halogen, $C_{1-5}$-haloalkoxy, $C_{1-6}$-alkoxy, aryl, $C_{1-4}$-dialkylamino, $C_{1-6}$-thioalkyl, thioaryl
or $R_4R_5$ together form an annulated phenyl
characterized in that ketimines of the formula (II)

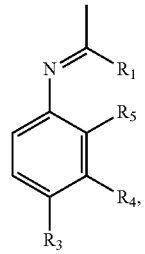

in which the radicals are as defined above,
are reacted with fluoroalkylamino reagents of the formula (III)

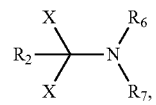

in which
X is F or Cl,
$R^6$ and $R^7$ are each independently selected from $C_{1-6}$-alkyl, $C_{3-8}$-cycloalkyl
in the presence of Lewis Acid.

DETAILED DESCRIPTION OF A PREFERRED EMBODIMENT

Preferred are compounds of the formula (I), (II) and (III), in which
$R^1$ is $CH_2F$, $CF_2H$, $CF_3$, $C_2F_5$,
$R^2$ is $CF_2H$, $CF_3$, $CFHCl$, $CF_3CFH$, $CFHOCF_3$,
$R^3$, $R^4$, $R^5$ are each independently selected from H, halogen, $CF_3O$, $N(CH_3)_2$, phenyl, $C_{1-6}$-thioalkyl, $C_{6-10}$-thioaryl, $C_{1-6}$-alkoxy, aryl, $C_{1-4}$-dialkylamino
or $R_4R_5$ together form an annulated phenyl,
X is F,
$R^6$, $R^7$ are each independently selected from $CH_3$, $C_2H_5$.

Most preferred are compounds of the formula (I), (II) and (III), in which
$R^1$ is $CF_2H$, $CF_3$,
$R^2$ is $CF_2H$, $CFHCl$, $CF_3CFH$, $R^3$ is H, F, $CF_3$, $CF_3O$, $N(CH_3)_2$,
$R^4$ is H, F, Cl, $OCH_3$, $OCF_3$, $N(CH_3)_2$, $CF_3$
or $R_4R_5$ together form an annulated phenyl,
$R^5$ is H, $OCH_3$, F, $OCF_3$, $CH_3$, phenyl, thiophenyl,
X is F,
$R^6$, $R^7$ are each independently selected from $CH_3$.

General Definitions

In the definitions of the symbols given in the above formulae, collective terms were used which are generally representative of the following substituents:

Halogen: fluorine, chlorine, bromine and iodine and preferably fluorine, chlorine, bromine and more preferably fluorine, chlorine.

Alkyl: saturated, straight-chain or branched hydrocarbyl radicals having 1 to 6 and preferably 1 to 3 carbon atoms, for example (but not limited to) $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. This definition also applies to alkyl as part of a composite substituent, for example cycloalkylalkyl, hydroxyalkyl etc., unless defined elsewhere like, for example, alkylthio, alkylsufinyl, alkylsulphonyl, haloalkyl or haloalkylthio. When the alkyl is at the end of a composite substituent, as, for example, in alkylcycloalkyl, the part of the composite substituent at the start, for example the cycloalkyl, may be mono- or polysubstituted, identically or different and in each case independently, by alkyl. The same also applies to composite substituents in which other radicals, for example alkenyl, alkynyl, hydroxyl, halogen, formyl, etc. are at the end.

Alkoxy: saturated, straight-chain or branched alkoxy radicals having 1 to 6 and more preferably 1 to 3 carbon atoms, for example (but not limited to) C1-C6-alkoxy, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropox. This definition also applies to alkoxy as part of a composite substituent, for example haloalkoxy, alkynylalkoxy, etc., unless defined elsewhere.

Alkylthio: saturated, straight-chain or branched alkylthio radicals having 1 to 6 and preferably 1 to 3 carbon atoms, for example (but not limited to) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio. This definition also applies to alkylthio as part of a composite substituent, for example haloalkylthio etc., unless defined elsewhere.

Cycloalkyl: monocyclic saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Haloalkyl: straight-chain or branched alkyl groups having 1 to 5 and more preferably 1 to 3 carbon atoms (as specified above), where some or all of the hydrogen atoms in these groups may be replaced by halogen atoms as specified above, for example (but not limited to) $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere.

Haloalkenyl and haloalkynyl are defined analogously to haloalkyl, except that, instead of alkyl groups, alkenyl and alkynyl groups are present as part of the substituent.

Haloalkoxy: straight-chain or branched alkoxy groups having 1 to 5 and more preferably 1 to 3 carbon atoms (as specified above), where some or all of the hydrogen atoms in these groups may be replaced by halogen atoms as specified above, for example (but not limited to) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, for example haloalkoxyalkyl etc., unless defined elsewhere.

PROCESS DESCRIPTION

The process is illustrated in Scheme 1:

Scheme 1:

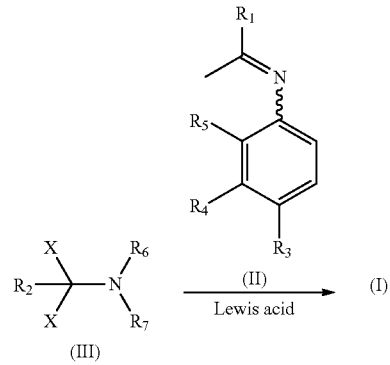

Quinoline derivatives of the formula (I) are prepared in that ketimines of the formula (II) are reacted with fluoroalkylamino reagents of the formula (III) in the presence of Lewis Acid.

Ketimines (II) can be prepared by the condensation of anilines (IV) and ketones (V) according to the literature procedure ((a) L. Troisi et al., *Tetrahedron*, 2013, 69, 3878-3884; (b) I. V. Kutovaya et al., *Eur. J. Org. Chem.*, 2015, 30, 6749-6761; (c) S. Prakash et al., *J. Fluorine Chem.*, 2007, 128, 587-594).

Scheme 2:

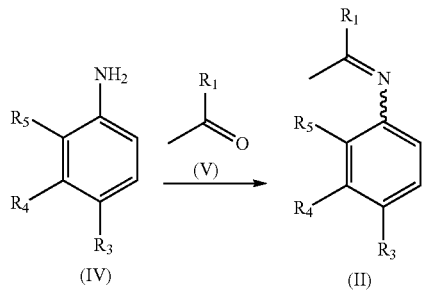

Fluoralkyamino reagents of the formula (III) are commercially available.

In a preferred embodiment of the process according to the invention, the fluoroalkylamino reagents (III) are first reacted with $BF_3$ or $AlCl_3$ according to WO 2008/022777 and then compound of the formula (II) is added in substance or dissolved in a suitable solvent.

Preferred is $BF_3$ as Lewis Acid. $BF_3$ can be used as a gas or as a solution/complex in ether or acetonitrile.

For the process according to the invention 1 to 2 mol, preferred 1 to 1.5 mol, most preferred 1 to 1.2 mol compound of formula (III) is reacted with 1 mol compound of formula (II).

The cyclization and formation of (I) is affected at temperatures of 0° C. to +80° C., preferably at temperatures of +20° C. to +70° C., more preferably at +30° C. to +70° C. and under standard pressure.

The reaction time is not critical and may, according to the batch size, be selected within a relatively wide range. Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, cyclohexane or methylcyclohexane, and very particular preference, for example, to acetonitrile, THF, acetonitrile, ether or dichloromethane.

After the reaction has ended, for example, the solvents are removed and the product is isolated by purification on flash chromatography.

EXAMPLE 1

N-(1,1,1-Trifluoropropan-2-ylidene)aniline (II-1)

Under argon atmosphere, an excess of cold 1,1,1-trifluoroacetone (2 eq., 2.39 g, 1.92 mL, 21.4 mmol) was added to aniline (IV-1) (1 eq., 1 g, 0.98 mL, 10.7 mmol) in anhydrous dichloromethane (20 mL) in presence of molecular sieves (MS) 4 Å. Then the reaction mixture was stirred for 3 h at room temperature. MS was then filtered off on celite and washed with ether. The filtrate was concentrated under reduce pressure to give the product (II-1) (1.74 g) as a brown oil in 87% yield. The compound was used without any further purification.

$^1$H NMR (400 MHz, $CDCl_3$; $Me_4Si$) δ=7.41-7.34 (m, 3,5-$CH_{arom}$), 7.21-7.14 (m, 4-$CH_{arom}$), 6.79 (dd, 2,6-$CH_{arom}$, $^3J_{H-H}$=8.4, $^4J_{H-H}$=1.1 Hz), 2.02 (s, $CH_3$) ppm.

$^{19}$F NMR (376 MHz, $CDCl_3$; $CFCl_3$) δ=−74.68 (s, $CF_3$) ppm.

$^{13}$C NMR (101 MHz, $CDCl_3$; $Me_4Si$) δ=157.41 (q, $CCF_3$, $^2J_{C-F}$=33.9 Hz), 147.72 (s, 1-$C_{arom}$), 129.33 (s, 3,5-$C_{arom}$), 125.29 (s, 4-$C_{arom}$), 119.87 (q, $CF_3$, $^1J_{C-F}$=278.4 Hz) 118.87 (s, 2,6-$C_{arom}$), 14.50 (s, $CH_3$) ppm.

EXAMPLE 2

2-Methoxy-N-(1,1,1-trifluoropropan-2-ylidene)aniline (II-2)

Under argon atmosphere, an excess of cold 1,1,1-trifluoroacetone (2 eq., 1.82 g, 1.46 mL, 16.2 mmol) was added to 2-methoxyaniline (IV-2) (1 eq., 1 g, 0.92 mL, 8.12 mmol) in anhydrous dichloromethane (16 mL) in presence of molecular sieves (MS) 4 Å. Then the reaction mixture was stirred for 21 h at room temperature. MS was then filtered off on celite and washed with ether. The filtrate was concentrated under reduce pressure to give the product (II-2) as a brown oil in 90% yield (1.59 g). The compound was used without any further purification.

$^1$H NMR (400 MHz, $CDCl_3$; $Me_4Si$) δ=7.16-7.12 (m, 4-$CH_{arom}$), 7.00-6.90 (m, 5,6-$CH_{arom}$), 6.78-6.75 (m, 3-$CH_{arom}$), 3.79-3.78 (m, $OCH_3$), 1.95 (s, $CH_3$) ppm.

$^{19}$F NMR (376 MHz, $CDCl_3$; $CFCl_3$) δ=−74.33-−74.42 (m, $CF_3$) ppm.

$^{13}$C NMR (101 MHz, $CDCl_3$; $Me_4Si$) δ=158.86 (q, $CCF_3$, $^2J_{C-F}$=33.7 Hz), 148.19 (s, $COCH_3$), 136.43 (s, 1-$C_{arom}$), 126.15 (s, 4-$C_{arom}$), 120.90 (s, 5-$C_{arom}$), 120.14 (s, 3-$C_{arom}$), 119.77 (q, $CF_3$, $^1J_{C-F}$=278.4 Hz), 111.78 (s, 6-$C_{arom}$), 55.51 (s, $OCH_3$), 14.90 (s, $CH_3$) ppm.

HRMS (ESI positive) for $C_{10}H_{11}F_3NO$ [M+]: calcd 218.0787; found 218.0773.

EXAMPLE 3

3-Methoxy-N-(1,1,1-trifluoropropan-2-ylidene)aniline (II-3)

Under argon atmosphere, an excess of cold 1,1,1-trifluoroacetone (2 eq., 1.82 g, 1.46 mL, 16.2 mmol) was added to 3-methoxyaniline (IV-3) (1 eq., 1 g, 0.91 mL, 8.12 mmol) in anhydrous dichloromethane (16 mL) in presence of molecular sieves (MS) 4 Å. Then the reaction mixture was stirred for 24 h at room temperature. MS was then filtered off on celite and washed with ether. The filtrate was concentrated under reduce pressure to give the product (II-3) as a brown oil in 92% yield (1.62 g). The compound was used without any further purification.

$^1$H NMR (400 MHz, $CDCl_3$; $Me_4Si$) δ=7.35-7.22 (m, 5-$CH_{arom}$), 6.79-6.70 (m, 4-$CH_{arom}$), 6.44-6.32 (m, 2,6-$CH_{arom}$), 3.79 (s, $OCH_3$), 2.05 (s, $CH_3$) ppm.

$^{19}$F NMR (376 MHz, $CDCl_3$; $CFCl_3$) δ=−74.81 (s, $CF_3$), −74.91 (s, $CF_3$) ppm [Z/E signal ratio 3:1].

$^{13}$C NMR (101 MHz, $CDCl_3$; $Me_4Si$) δ=160.50 (s, $COCH_3$), 157.56 (q, $CCF_3$, $^2J_{C-F}$=33.9 Hz), 148.95 (s, 1-$C_{arom}$), 130.08 (S, 5-$C_{arom}$), 119.78 (q, $CF_3$, $^1J_{C-F}$=278.2 Hz), 110.60 (s, 4,6-$C_{arom}$), 104.49 (s, 2-$C_{arom}$), 54.91 (s, $OCH_3$), 14.01 (s, $CH_3$) ppm.

HRMS (ESI positive) for $C_{10}H_{11}F_3NO$ [M+H]: calcd 218.0787; found 218.0818.

EXAMPLE 4

4-Methoxy-N-(1,1,1-trifluoropropan-2-ylidene)aniline (II-4)

Under argon atmosphere, an excess of cold 1,1,1-trifluoroacetone (2 eq., 1.84 g, 1.47 mL, 16.4 mmol) was added to 4-methoxyaniline (IV-4) (1 eq., 1.01 g, 8.2 mmol) in anhydrous dichloromethane (16 mL) in presence of molecular sieves (MS) 4 Å. Then the reaction mixture was stirred for 20 h at room temperature. MS was then filtered off on celite and washed with ether. The filtrate was concentrated under reduce pressure to give the product (II-4) as a brown oil in 93% yield (1.65 g). The compound was used without any further purification.

$^1$H NMR (400 MHz, CDCl$_3$; Me$_4$Si) δ=6.86 (m, AA', 2,6-CH$_{arom}$), 6.73 (m, BB', 3,5-CH$_{arom}$), 3.75-3.71 (m, OCH$_3$), 2.03-2.00 (m, CH$_3$) ppm.

$^{19}$F NMR (376 MHz, CDCl$_3$; CFCl$_3$) δ=−74.54--74.61 (m, CF$_3$), −74.61--74.73 (m, CF$_3$) ppm [Z/E signal ratio 1:1].

$^{13}$C NMR (101 MHz, CDCl$_3$; Me$_4$Si) δ=157.51 (s, OCH$_3$), 156.53 (q, CCF$_3$, $^2J_{C-F}$=33.5 Hz), 140.36 (s, 1-C$_{arom}$), 120.85 (s, 3,5-C$_{arom}$), 119.96 (q, CF$_3$, $^1J_{C-F}$=278.1 Hz), 114.31 (s, 2,6-C$_{arom}$), 55.09 (s, OCH$_3$), 13.99 (s, CH$_3$) ppm.

HRMS (ESI positive) for C$_{10}$H$_{11}$F$_3$NO [M+H]: calcd 218.0787; found 218.0815.

EXAMPLE 5

2-Fluoro-N-(1,1,1-trifluoropropan-2-ylidene)aniline (II-5)

Under argon atmosphere, an excess of cold 1,1,1-trifluoroacetone (2 eq., 4.03 g, 3.23 mL, 36 mmol) was added to 2-fluoroaniline (IV-5) (1 eq., 2 g, 1.74 mL, 18 mmol) in anhydrous dichloromethane (30 mL) in presence of molecular sieves (MS) 4 Å. Then the reaction mixture was stirred for 16 h at room temperature. MS was then filtered off on celite and washed with ether. The filtrate was concentrated under reduce pressure to give the product (II-5) as a brown oil in 70% yield (2.58 g). The compound was used without any further purification.

$^1$H NMR (400 MHz, CDCl$_3$; Me$_4$Si) δ=7.21-7.07 (m, 4,5,6-CH$_{arom}$), 6.93-6.86 (m, 3-CH$_{arom}$), 2.02 (s, CH$_3$) ppm.

$^{19}$F NMR (376 MHz, CDCl$_3$; CFCl$_3$) δ=−74.65 (s, CF$_3$), −126.51--126.58 (m, F) ppm.

$^{13}$C NMR (101 MHz, CDCl$_3$; Me$_4$Si) δ=160.40 (qd, CCF$_3$, $^2J_{C-F}$=34.1, $^4J_{C-F}$=0.5 Hz), 151.01 (d, CF, $^1J_{C-F}$=246.3 Hz), 134.91 (d, 1-C$_{arom}$, $^2J_{C-F}$=12.8 Hz), 126.57 (d, 4-C$_{arom}$, $^3J_{C-F}$=7.3 Hz), 124.59 (d, 5-C$_{arom}$, $^4J_{C-F}$=3.8 Hz), 121.68 (d, 6-C$_{arom}$, $^3J_{C-F}$=1.1 Hz), 119.53 (q, CF$_3$, $^1J_{C-F}$=278.2 Hz), 116.18 (d, 3-C$_{arom}$, $^2J_{C-F}$=19.7 Hz), 15.01 (s, CH$_3$) ppm.

HRMS (ESI positive) for C$_9$H$_8$F$_4$N [M+H]: calcd 206.0587; found 206.0590.

EXAMPLE 6

3-Fluoro-N-(1,1,1-trifluoropropan-2-ylidene)aniline (II-6)

Under argon atmosphere, an excess of cold 1,1,1-trifluoroacetone (2 eq., 2.02 g, 1.61 mL, 18 mmol) was added to 3-fluoroaniline (IV-6) (1 eq., 1 g, 0.87 mL, 9 mmol) in anhydrous dichloromethane (17 mL) in presence of molecular sieves (MS) 4 Å. Then the reaction mixture was stirred for 48 h at room temperature. MS was then filtered off on celite and washed with ether. The filtrate was concentrated under reduce pressure to give the product (II-6) as a brown oil in 62% yield (1.14 g). The compound was used without any further purification.

$^1$H NMR (400 MHz, CDCl$_3$; Me$_4$Si) δ=7.36-7.28 (m, 5-CH$_{arom}$), 6.90-6.82 (m, 4-CH$_{arom}$), 6.57-6.49 (m, 2,6-CH$_{arom}$), 2.02 (s, CH$_3$) ppm.

$^{19}$F NMR (376 MHz, CDCl$_3$; CFCl$_3$) δ=−74.91 (s, CF$_3$), −74.99 (s, CF$_3$), −111.78--111.92 (m, F) ppm [Z/E signal].

$^{13}$C NMR (101 MHz, CDCl$_3$; Me$_4$Si) δ=163.44 (d, CF, $^1J_{C-F}$=247.2 Hz), 158.64 (q, CCF$_3$, $^2J_{C-F}$=34.3 Hz), 149.33 (d, 1-C$_{arom}$, $^3J_{C-F}$=9.1 Hz), 130.70 (d, 5-C$_{arom}$, $^3J_{C-F}$=9.2 Hz), 119.56 (q, CF$_3$, $^1J_{C-F}$=278.3 Hz), 114.45 (d, 6-C$_{arom}$, $^4J_{C-F}$=2.9 Hz), 112 (d, 4-C$_{arom}$, $^2J_{C-F}$=21.3 Hz), 106.38 (d, 2-C$_{arom}$, $^2J_{C-F}$=24.1 Hz), 14.36 (s, CH$_3$) ppm.

HRMS (ESI positive) for C$_9$H$_8$F$_4$N [M+H]: calcd 206.0587; found 206.0572.

EXAMPLE 7

4-Fluoro-N-(1,1,1-trifluoropropan-2-ylidene)aniline (II-7)

Under argon atmosphere, an excess of cold 1,1,1-trifluoroacetone (2 eq., 2.33 g, 1.87 mL, 20.8 mmol) was added to 4-fluoroaniline (IV-7) (1 eq., 1.16 g, 1 mL, 10.4 mmol) in anhydrous dichloromethane (20 mL) in presence of molecular sieves (MS) 4 Å. Then the reaction mixture was stirred for 13 h at room temperature. MS was then filtered off on celite and washed with ether. The filtrate was concentrated under reduce pressure to give the product (II-7) as a brown oil in 93% yield (1.97 g). The compound was used without any further purification.

$^1$H NMR (400 MHz, CDCl$_3$; Me$_4$Si) δ=7.10-7.03 (m, 3,5-CH$_{arom}$), 6.79-6.73 (m, 2,6-CH$_{arom}$), 2.03 (s, CH$_3$) ppm.

$^{19}$F NMR (376 MHz, CDCl$_3$; CFCl$_3$) δ=−74.77 (s, CF$_3$), −74.79 (s, CF$_3$), −117.79--118.66 (m, F) ppm [Z/E signal].

$^{13}$C NMR (101 MHz, CDCl$_3$; Me$_4$Si) δ=160.39 (d, CF, $^1J_{C-F}$=244.1 Hz), 158.01 (qd, CCF$_3$, $^2J_{C-F}$=33.9, $^6J_{C-F}$=1.1 Hz), 143.59 (d, 1-C$_{arom}$, $^4J_{C-F}$=2.7 Hz), 120.68 (d, 2,6-C$_{arom}$, $^3J_{C-F}$=8.2 Hz), 119.68 (q, CF$_3$, $^1J_{C-F}$=278.2 Hz), 115.98 (d, 3,5-C$_{arom}$, $^2J_{C-F}$=22.8 Hz), 14.38 (s, CH$_3$) ppm.

LCMS: RT: 1.82-1.87 min; E$^+$=223 [M+H$_2$O].

EXAMPLE 8

2-(Trifluoromethoxy)-N-(1,1,1-trifluoropropan-2-ylidene) aniline (II-8)

Under argon atmosphere, an excess of cold 1,1,1-trifluoroacetone (2 eq., 2.53 g, 2.02 mL, 22.6 mmol) was added to product 2-(trifluoromethoxy)aniline (IV-8) (1 eq., 2 g, 1.54 mL, 11.3 mmol) in anhydrous dichloromethane (23 mL) in presence of molecular sieves (MS) 4 Å. Then the reaction mixture was stirred for 24 h at room temperature. MS was then filtered off on celite and washed with ether. The filtrate was concentrated under reduce pressure to give the product (II-8) as a brown oil in 15% yield (448 mg) in mixture with starting material (6/1 IV-8:II-8). The compound was used without any further purification.

$^1$H NMR (400 MHz, CDCl$_3$; Me$_4$Si) δ=7.35-7.30 (m, 4,6-CH$_{arom}$), 7.24-7.20 (m, 5-CH$_{arom}$), 6.86 (dd, $^3J_{H-H}$=8.1, $^4J_{H-H}$=1.5 Hz, 3-CH$_{arom}$), 2.02 (s, CH$_3$) ppm.

$^{19}$F NMR (376 MHz, CDCl$_3$; CFCl$_3$) δ=−58.19 (s, OCF$_3$), −87.18 (s, CH$_3$) ppm.

HRMS (ESI positive) for C$_{10}$H$_8$F$_6$NO [M+H]: calcd 272.0505; found 272.0493.

EXAMPLE 9

3-(Trifluoromethoxy)-N-(1,1,1-trifluoropropan-2-ylidene) aniline (II-9)

Under argon atmosphere, an excess of cold 1,1,1-trifluoroacetone (2 eq., 1.27 g, 1.01 mL, 11.3 mmol) was added to 3-(trifluoromethoxy)aniline (IV-9) (1 eq., 1 g, 0.76 mL, 5.65 mmol) in anhydrous dichloromethane (11 mL) in presence of molecular sieves (MS) 4 Å. Then the reaction mixture was stirred for 48 h at room temperature. MS was then filtered off on celite and washed with ether. The filtrate was concentrated under reduce pressure to give the product (II-9) as a brown oil in 82% yield (1.25 g). The compound was used without any further purification.

¹H NMR (400 MHz, CDCl₃; Me₄Si) δ=7.40 (t, 5-CH$_{arom}$, ³J$_{H-H}$=8.1 Hz), 7.04 (d, 4-CH$_{arom}$, ³J$_{H-H}$=8.3 Hz), 6.71 (d, 6-CH$_{arom}$, ³J$_{H-H}$=7.9 Hz), 6.68 (s, 2-CH$_{arom}$), 2.03 (s, CH₃) ppm.
¹⁹F NMR (376 MHz, CDCl₃; CFCl₃) δ=−58.08 (s, OCF₃), −74.91 (s, CH₃) ppm.
¹³C NMR (101 MHz, CDCl₃; Me₄Si) δ=158.85 (q, CCF₃, ²J$_{C-F}$=34.3 Hz), 150.05 (q, COCF₃, ³J$_{C-F}$=2.02 Hz), 149.12 (s, 1-C$_{arom}$), 130.75 (s, 5-C$_{arom}$), 120.41 (q, OCF₃, ¹J$_{C-F}$=258.2 Hz), 119.49 (q, CF₃, ¹J$_{C-F}$=278.3 Hz), 117.27 (s, 4-C$_{arom}$), 116.96 (s, 6-C$_{arom}$), 111.58 (s, 2-C$_{arom}$), 14.52 (s, CH₃) ppm.
HRMS (ESI positive) for C₁₀H₈F₆NO [M+H]: calcd 272.0505; found 272.0488.

EXAMPLE 10

4-(Trifluoromethoxy)-N-(1,1,1-trifluoropropan-2-ylidene)aniline (II-10)

Under argon atmosphere, an excess of cold 1,1,1-trifluoroacetone (2 eq., 2.53 g, 2.02 mL, 22.6 mmol) was added to 4-(trifluoromethoxy)aniline (IV-10) (1 eq., 2 g, 1.53 mL, 11.3 mmol) in anhydrous dichloromethane (23 mL) in presence of molecular sieves (MS) 4 Å. Then the reaction mixture was stirred for 48 h at room temperature. MS was then filtered off on celite and washed with ether. The filtrate was concentrated under reduce pressure to give the product (II-10) as a brown oil in 93% yield (2.85 g). The compound was used without any further purification.
¹H NMR (400 MHz, CDCl₃; Me₄Si) [Z/E signal ratio 4.35:0.65]. δ=7.17 (d, 2,6-CH$_{arom}$, ³J$_{H-H}$=8.8 Hz), 6.95 (d, 2',6'-CH$_{arom}$, ³J$_{H-H}$=8.8 Hz), 6.73 (d, 3,5-CH$_{arom}$, ³J$_{H-H}$=8.8 Hz), 6.61 (d, 3',5'-CH$_{arom}$, ³J$_{H-H}$=8.8 Hz), 1.96 (s, CH₃), 1.96 (s, CH₃') ppm.
¹⁹F NMR (376 MHz, CDCl₃; CFCl₃) δ=−58.40--58.67 (m, OCF₃), −74.89--75.12 (m, CF₃) ppm.
¹³C NMR (101 MHz, CDCl₃; Me₄Si) δ=158.94 (q, CCF₃, ²J$_{C-F}$=34.3 Hz), 146.84 (q, COCF₃, ³J$_{C-F}$=2.02 Hz), 146.15 (s, 1-C$_{arom}$), 122.26 (s, 2,6-C$_{arom}$), 120.31 (s, 3,5-C$_{arom}$), 120.76 (q, OCF₃, ¹J$_{C-F}$=256.8 Hz), 119.79 (q, CF₃, ¹J$_{C-F}$=278.2 Hz), 14.46 (s, CH₃) ppm.
HRMS (ESI positive) for C₁₀H₈F₆NO [M+H]: calcd 272.0505; found 272.0496.

EXAMPLE 11

1-N,N-Dimethyl-4-N-(1,1,1-trifluoropropan-2-ylidene)benzene-1,4-diamine (II-11)

Under argon atmosphere, an excess of cold 1,1,1-trifluoroacetone (2 eq., 1.66 g, 1.32 mL, 14.8 mmol) was added to N,N-dimethyl-1,4-benzenediamine (IV-11) (1 eq., 1.01 g, 0.92 mL, 7.39 mmol) in anhydrous dichloromethane (15 mL) in presence of molecular sieves (MS) 4 Å. Then the reaction mixture was stirred for 24 h at room temperature. MS was then filtered off on celite and washed with ether. The filtrate was concentrated under reduce pressure to give the product (II-11) as a brown oil in 80% yield (1.36 g). The compound was used without any further purification.
¹H NMR (400 MHz, CDCl₃; Me₄Si) δ=6.83 (m, AA', 2,6-CH$_{arom}$), 6.74 (m, BB', 3,5-CH$_{arom}$), 2.96 (s, N(CH₃)₂), 2.11 (s, CH₃) ppm.
¹⁹F NMR (376 MHz, CDCl₃; CFCl₃) δ=−74.19 (s, CF₃) ppm.
¹³C NMR (101 MHz, CDCl₃; Me₄Si) δ=154.86 (q, CCF₃, ²J$_{C-F}$=33.3 Hz), 148.94 (s, CN(CH₃)₂), 136.65 (s, 1-C$_{arom}$), 121.94 (s, 2,6-C$_{arom}$), 120.15 (q, CF₃, ¹J$_{C-F}$=278.0 Hz), 112.86 (s, 3,5-C$_{arom}$), 40.84 (s, N(CH₃)₂), 14.67 (s, CH₃) ppm.
HRMS (ESI positive) for C₁₁H₁₄F₃N₂ [M+H]: calcd 231.1104; found 231.1125.

EXAMPLE 12

3-Fluoro-2-methyl-N-(1,1,1-trifluoropropan-2-ylidene)aniline (II-12)

Under argon atmosphere, an excess of cold 1,1,1-trifluoroacetone (2 eq., 3.58 g, 2.87 mL, 32 mmol) was added to 3-fluoro-2-methylaniline (IV-12) (1 eq., 2 g, 1.82 mL, 16 mmol) in anhydrous dichloromethane (30 mL) in presence of molecular sieves (MS) 4 Å. Then the reaction mixture was stirred for 26 h at room temperature. MS was then filtered off on celite and washed with ether. The filtrate was concentrated under reduce pressure to give the product (II-12) as a brown oil in 57% yield (2.01 g) in mixture with the starting material and the resulting compound from ketone autocondensation. The compound was used without any further purification.
¹H NMR (400 MHz, CDCl₃; Me₄Si) δ=7.17 (dd, 4-CH$_{arom}$, ³J$_{H-F}$=14.3, ³J$_{H-H}$=7.8 Hz), 6.97 (dd, 5-CH$_{arom}$, ⁴J$_{H-F}$=14.8, ³J$_{H-H}$=7.8 Hz), 6.43 (d, 6-CH$_{arom}$, ³J$_{H-H}$=7.9 Hz), 2.01 (s, C$_{arom}$CH₃), 1.99 (s, CH₃) ppm.
¹⁹F NMR (376 MHz, CDCl₃; CFCl₃) δ=−74.56 (s, CF₃), −115.94 (s, F) ppm.
HRMS (ESI positive) for C₁₀H₁₀F₄N [M+H]: calcd 220.0744; found 220.0746.

EXAMPLE 13

3-Chloro-2-methyl-N-(1,1,1-trifluoropropan-2-ylidene)aniline (II-13)

Under argon atmosphere, an excess of cold 1,1,1-trifluoroacetone (2 eq., 3.17 g, 2.53 mL, 28.2 mmol) was added to 3-chloro-2-methylaniline (IV-13) (1 eq., 2 g, 1.71 mL, 14.1 mmol) in anhydrous dichloromethane (26 mL) in presence of molecular sieves (MS) 4 Å. Then the reaction mixture was stirred for 26 h at room temperature. MS was then filtered off on celite and washed with ether. The filtrate was concentrated under reduce pressure to give the product (II-13) as a brown oil in 50% yield (1.67 g) in mixture with the starting material and the resulting compound from ketone autocondensation. The compound was used without any further purification.
¹H NMR (400 MHz, CDCl₃; Me₄Si) δ=7.22 (dd, 4-CH$_{arom}$, ³J$_{H-H}$=8.0, ⁴J$_{H-H}$=1.0 Hz), 7.14 (t, 5-CH$_{arom}$, ³J$_{H-H}$=7.9 Hz), 6.53 (dd, 6-CH$_{arom}$, ³J$_{H-H}$=7.8, ⁴J$_{H-H}$=0.8 Hz), 2.14 (s, C$_{arom}$CH₃), 1.98 (s, CH₃) ppm.
¹⁹F NMR (376 MHz, CDCl₃; CFCl₃) δ=−74.51 (s, CF₃) ppm.
HRMS (ESI positive) for C₁₀H₁₀F₃NCl [M+H]: calcd 236.0448; found 236.0462.

EXAMPLE 14

N-(1,1-Difluoropropan-2-ylidene)aniline (II-14)

Under argon atmosphere, an excess of cold 1,1-difluoroacetone (1.07 eq., 5800 mg, 5 mL, 58.2 mmol) was added to aniline (IV-1) (1 eq., 5106 mg, 5 mL, 54.6 mmol) in anhydrous dichloromethane (20 mL) in presence of molecular sieves (MS) 4 Å. Then the reaction mixture was stirred for 3 h at room temperature. MS was then filtered off on celite and washed with ether. The filtrate was concentrated under reduce pressure to give the product (II-14) as a brown oil in 96% yield (8.72 g). The compound was used without any further purification.

$^1$H NMR (400 MHz, CDCl$_3$; Me$_4$Si) δ=7.37 (t, 3,5-CH$_{arom}$, $^3J_{H-H}$=7.8 Hz), 7.16 (t, 4-CH$_{arom}$, $^3J_{H-H}$=7.2 Hz), 6.78 (d, 2,6-CH$_{arom}$, $^3J_{H-H}$=7.4 Hz), 6.07 (t, CHF$_2$, $^2J_{H-F}$=55.6 Hz), 1.95 (s, CH$_3$) ppm.

$^{19}$F NMR (376 MHz, CDCl$_3$; CFCl$_3$) δ=−121.27 (d, CHF$_2$, $^2J_{F-H}$=55.5 Hz) ppm.

$^{13}$C NMR (101 MHz, CDCl$_3$; Me$_4$Si) δ=163.54 (t, CCHF$_2$, $^2J_{C-F}$=28.8 Hz), 148.47 (s, 1-C$_{arom}$), 129.12 (s, 3,5-C$_{arom}$), 124.86 (s, 4-C$_{arom}$), 119.01 (s, 2,6-C$_{arom}$), 114.96 (t, CHF$_2$, $^1J_{C-F}$=243.0 Hz), 12.65 (s, CH$_3$) ppm.

HRMS (ESI positive) for C$_9$H$_{10}$F$_2$N [M+H]: calcd 170.0774; found 170.0776.

EXAMPLE 15

N-(1,1-Difluoropropan-2-ylidene)-2-methoxyaniline (II-15)

Under argon atmosphere, an excess of cold 1,1-difluoroacetone (2 eq., 1.53 g, 1.32 mL, 16.2 mmol) was added to 2-methoxyaniline (IV-2) (1 eq., 1 g, 0.92 mL, 8.12 mmol) in anhydrous dichloromethane (16 mL) in presence of molecular sieves (MS) 4 Å. Then the reaction mixture was stirred for 5 h at room temperature. MS was then filtered off on celite and washed with ether. The filtrate was concentrated under reduce pressure to give the product (II-15) as a brown oil in 98% yield (1.59 g). The compound was used without any further purification.

$^1$H NMR (400 MHz, CDCl$_3$; Me$_4$Si) δ=7.14 (td, 4-CH$_{arom}$, $^3J_{H-H}$=7.8, $^4J_{H-H}$=1.6 Hz), 6.99-6.92 (m, 5,6-CH$_{arom}$), 6.74 (dd, 3-CH$_{arom}$, $^3J_{H-H}$=7.6, $^4J_{H-H}$=1.6 Hz), 6.12 (t, CHF$_2$, $^2J_{H-F}$=55.6 Hz), 3.80 (s, OCH$_3$), 1.89 (s, CH$_3$) ppm.

$^{19}$F NMR (376 MHz, CDCl$_3$; CFCl$_3$) δ=−120.86 (d, CHF$_2$, $^2J_{F-H}$=55.5 Hz) ppm.

$^{13}$C NMR (101 MHz, CDCl$_3$; Me$_4$Si) δ=164.88 (t, CCHF$_2$, $^2J_{C-F}$=28.6 Hz), 148.64 (s, COCH$_3$), 137.30 (s, 1-C$_{arom}$), 125.75 (s, 4-C$_{arom}$), 120.87 (s, 5-C$_{arom}$), 120.17 (s, 3-C$_{arom}$), 114.83 (t, CHF$_2$, $^1J_{C-F}$=242.8 Hz), 111.65 (s, 6-C$_{arom}$), 55.56 (s, OCH$_3$), 13.11 (s, CH$_3$) ppm.

HRMS (ESI positive) for C$_{10}$H$_{12}$F$_2$NO [M+H]: calcd 200.0881; found 200.0875.

EXAMPLE 16

N-(1,1-Difluoropropan-2-ylidene)-3-methoxyaniline (II-16)

Under argon atmosphere, an excess of cold 1,1-difluoroacetone (2 eq., 1.53 g, 1.32 mL, 16.2 mmol) was added to 3-methoxyaniline (IV-3) (1 eq., 1 g, 0.91 mL, 8.12 mmol) in anhydrous dichloromethane (16 mL) in presence of molecular sieves (MS) 4 Å. Then the reaction mixture was stirred for 4 h at room temperature. MS was then filtered off on celite and washed with ether. The filtrate was concentrated under reduce pressure to give the product (II-16) as a brown oil in 98% yield (1.58 g). The compound was used without any further purification.

$^1$H NMR (400 MHz, CDCl$_3$; Me$_4$Si) δ=7.30-7.26 (m, 5-CH$_{arom}$), 6.75-6.73 (m, 4-CH$_{arom}$), 6.39-6.38 (m, 2,6-CH$_{arom}$), 6.10 (t, CHF2, $^2J_{H-F}$=55.6 Hz), 3.83-3.80 (m, OCH$_3$), 1.99-1.97 (m, CH$_3$) ppm.

$^{19}$F NMR (376 MHz, CDCl$_3$; CFCl$_3$) [Z/E signal ratio 27:73]. δ=−121.33 (d, CHF$_2$, $^2J_{F-H}$=55.6 Hz), −121.37 (d, CHF$_2$, $^2J_{F-H}$=55.6 Hz) ppm.

$^{13}$C NMR (101 MHz, CDCl$_3$; Me$_4$Si) δ=163.41 (t, CCHF$_2$, $^2J_{C-F}$=28.7 Hz), 160.41 (s, COCH$_3$), 149.81 (s, 1-C$_{arom}$), 129.95 (S, 5-C$_{arom}$), 114.89 (t, CHF$_2$, $^1J_{C-F}$=242.9 Hz), 110.92 (s, 6-C$_{arom}$), 110.25 (s, 4-C$_{arom}$), 104.65 (s, 2-C$_{arom}$), 55.01 (s, OCH$_3$), 12.35 (s, CH$_3$) ppm.

HRMS (ESI positive) for C$_{10}$H$_{12}$F$_2$NO [M+H]: calcd 200.0881; found 200.0884.

EXAMPLE 17

N-(1,1-Difluoropropan-2-ylidene)-4-methoxyaniline (II-17)

Under argon atmosphere, an excess of cold 1,1-difluoroacetone (2 eq., 1.68 g, 1.44 mL, 17.8 mmol) was added to 4-methoxyaniline (IV-4) (1 eq., 1.1 g, 8.91 mmol) in anhydrous dichloromethane (16 mL) in presence of molecular sieves (MS) 4 Å. Then the reaction mixture was stirred for 5 h at room temperature. MS was then filtered off on celite and washed with ether. The filtrate was concentrated under reduce pressure to give the product (II-17) as a brown oil in 98% yield (1.74 g). The compound was used without any further purification.

$^1$H NMR (400 MHz, CDCl$_3$; Me$_4$Si) δ=6.87 (m, AA', 2,6-CH$_{arom}$), 6.73 (m, BB', 3,5-CH$_{arom}$), 6.02 (t, CHF$_2$, $^2J_{H-F}$=55.7 Hz), 3.77-3.69 (m, OCH$_3$), 1.94-1.93 (m, CH$_3$) ppm.

$^{19}$F NMR (376 MHz, CDCl$_3$; CFCl$_3$) δ=−121.11 (dd, CHF$_2$, $^2J_{F-H}$=55.8, $^4J_{F-H}$=4.0 Hz) ppm.

$^{13}$C NMR (101 MHz, CDCl$_3$; Me$_4$Si) δ=162.77 (t, CCHF$_2$, $^2J_{C-F}$=29.4 Hz), 157.11 (s, COCH$_3$), 141.22 (s, 1-C$_{arom}$), 120.80 (s, 3,5-C$_{arom}$), 115.23 (t, CHF$_2$, $^1J_{C-F}$=242.7 Hz), 114.21 (s, 2,6-C$_{arom}$), 55.11 (s, OCH$_3$), 12.26 (s, CH$_3$) ppm.

HRMS (ESI positive) for C$_{10}$H$_{12}$F$_2$NO [M+H]: calcd 200.0881; found 200.0893.

EXAMPLE 18

N-(1,1-Difluoropropan-2-ylidene)-2-fluoroaniline (II-18)

Under argon atmosphere, an excess of cold 1,1-difluoroacetone (2 eq., 3.39 g, 2.92 mL, 36 mmol) was added to 2-fluoroaniline (IV-5) (1 eq., 2 g, 1.74 mL, 18 mmol) in anhydrous dichloromethane (30 mL) in presence of molecular sieves (MS) 4 Å. Then the reaction mixture was stirred for 4 h at room temperature. MS was then filtered off on celite and washed with ether. The filtrate was concentrated under reduce pressure to give the product (II-18) as a brown oil in 78% yield (2.62 g). The compound was used without any further purification.

$^1$H NMR (400 MHz, CDCl$_3$; Me$_4$Si) δ=7.19-7.08 (m, 4,5,6-CH$_{arom}$), 6.90-6.82 (m, 3-CH$_{arom}$), 6.10 (t, CHF$_2$, $^2J_{H-F}$=55.5 Hz), 1.99-1.91 (m, CH$_3$) ppm.

$^{19}$F NMR (376 MHz, CDCl$_3$; CFCl$_3$) δ=−121.24 (d, CHF$_2$, $^2J_{F-H}$=55.5 Hz), −126.63 (s, F) ppm.

$^{13}$C NMR (101 MHz, CDCl$_3$; Me$_4$Si) δ=166.37 (t, CCHF$_2$, $^2J_{C-F}$=28.9 Hz), 151.51 (d, CF, $^1J_{C-F}$=245.8 Hz), 135.82 (d, 1-C$_{arom}$, $^2J_{C-F}$=13.0 Hz), 126.07 (d, 4-C$_{arom}$, $^3J_{C-F}$=7.3 Hz), 124.48 (d, 5-C$_{arom}$, $^4J_{C-F}$=3.8 Hz), 121.72 (s, 6-C$_{arom}$), 116.11 (d, 3-C$_{arom}$, $^2J_{C-F}$=19.8 Hz), 114.49 (t, CHF$_2$, $^1J_{C-F}$=243.0 Hz), 13.14 (s, CH$_3$) ppm.

HRMS (ESI positive) for C$_9$H$_9$F$_3$N [M+H]: calcd 188.0682; found 188.0687.

EXAMPLE 19

N-(1,1-Difluoropropan-2-ylidene)-3-fluoroaniline (II-19)

Under argon atmosphere, an excess of cold 1,1-difluoroacetone (2 eq., 1.69 g, 1.46 mL, 18 mmol) was added to 3-fluoroaniline (IV-6) (1 eq., 1 g, 0.87 mL, 9 mmol) in anhydrous dichloromethane (17 mL) in presence of molecular sieves (MS) 4 Å. Then the reaction mixture was stirred for 5 h at room temperature. MS was then filtered off on celite and washed with ether. The filtrate was concentrated under reduce pressure to give the product (II-19) as a brown oil in 91% yield (1.53 g). The compound was used without any further purification.

$^1$H NMR (400 MHz, CDCl$_3$; Me$_4$Si) δ=7.33-7.28 (m, 5-CH$_{arom}$), 6.84 (td, 4-CH$_{arom}$, $^3J_{H-H}$=8.5, $^4J_{H-H}$=2.5 Hz), 6.55-6.49 (m, 2,6-CH$_{arom}$), 6.03 (t, CHF$_2$, $^2J_{H-F}$=55.5 Hz), 1.94 (s, CH$_3$) ppm.

$^{19}$F NMR (376 MHz, CDCl$_3$; CFCl$_3$) δ=−111.96-−112.07 (m, F), −121.51 (d, CHF$_2$, $^2J_{F-H}$=55.4 Hz) ppm.

$^{13}$C NMR (101 MHz, CDCl$_3$; Me$_4$Si) δ=164.38 (t, CCHF$_2$, $^2J_{C-F}$=28.9 Hz), 163.35 (d, CF, $^1J_{C-F}$=247.45 Hz), 150.28 (d, 1-C$_{arom}$, $^3J_{C-F}$=9.2 Hz), 130.63 (d, 5-C$_{arom}$, $^3J_{C-F}$=9.2 Hz), 114.57 (t, CHF$_2$, $^1J_{C-F}$=242.4 Hz), 114.48 (d, 6-C$_{arom}$, $^4J_{C-F}$=2.9 Hz), 111.38 (d, 4-C$_{arom}$, $^2J_{C-F}$=21.3 Hz), 106.36 (d, 2-C$_{arom}$, $^2J_{C-F}$=23.7 Hz), 12.65 (s, CH$_3$) ppm.

HRMS (ESI positive) for C$_9$H$_9$F$_3$N [M+H]: calcd 188.0682; found 188.0672.

EXAMPLE 20

N-(1,1-Difluoropropan-2-ylidene)-4-fluoroaniline (II-20)

Under argon atmosphere, an excess of cold 1,1-difluoroacetone (2 eq., 1.57 g, 1.35 mL, 16.7 mmol) was added to 4-fluoroaniline (IV-7) (1 eq., 0.926 g, 0.8 mL, 8.33 mmol) in anhydrous dichloromethane (20 mL) in presence of molecular sieves (MS) 4 Å. Then the reaction mixture was stirred for 3 h at room temperature. MS was then filtered off on celite and washed with ether. The filtrate was concentrated under reduce pressure to give the product (II-20) as a brown oil in 83% yield (1.29 g). The compound was used without any further purification.

$^1$H NMR (400 MHz, CDCl$_3$; Me$_4$Si) δ=7.04 (t, 2,6-CH$_{arom}$, $^3J_{H-H}$=8.7 Hz), 6.75-6.72 (m, 3,5-CH$_{arom}$), 6.02 (t, CHF$_2$, $^2J_{H-F}$=55.6 Hz), 1.94 (s, CH$_3$) ppm.

$^{19}$F NMR (376 MHz, CDCl$_3$; CFCl$_3$) δ=−118.69-−119.06 (m, F), −121.38 (dd, CHF$_2$, $^2J_{F-H}$=55.6, $^4J_{F-H}$=2.6 Hz) ppm.

$^{13}$C NMR (101 MHz, CDCl$_3$; Me$_4$Si) δ=164.10 (t, CCHF$_2$, $^2J_{C-F}$=28.2 Hz), 160.27 (d, CF, $^1J_{C-F}$=243.3 Hz), 144.44 (d, 1-C$_{arom}$, $^4J_{C-F}$=1.2), 120.60 (d, 2,6-C$_{arom}$, $^3J_{C-F}$=8.1 Hz), 115.86 (d, 3,5-C$_{arom}$, $^2J_{C-F}$=22.6 Hz), 114.82 (t, CHF$_2$, $^1J_{C-F}$=243.0 Hz), 12.57 (s, CH$_3$) ppm.

HRMS (ESI negative) for C$_9$H$_7$F$_3$N [M−H]: calcd 186.0525; found 186.0544.

EXAMPLE 21

N-(1,1-Difluoropropan-2-ylidene)-2-(trifluoromethoxy)aniline (II-21)

Under argon atmosphere, an excess of cold 1,1-difluoroacetone (2 eq., 2.12 g, 1.83 mL, 22.6 mmol) was added to 2-(trifluoromethoxy)aniline (IV-8) (1 eq., 2 g, 1.54 mL, 11.3 mmol) in anhydrous dichloromethane (23 mL) in presence of molecular sieves (MS) 4 Å. Then the reaction mixture was stirred for 5 h at room temperature. MS was then filtered off on celite and washed with ether. The filtrate was concentrated under reduce pressure to give the product (II-21) as a brown oil in 75% yield (2.13 g). The compound was used without any further purification.

$^1$H NMR (400 MHz, CDCl$_3$; Me$_4$Si) δ=7.27-7.18 (m, 4,6-CH$_{arom}$), 7.12-7.06 (m, 5-CH$_{arom}$), 6.78-6.73 (m, 3-CH$_{arom}$), 6.03 (t, CHF$_2$, $^2J_{H-F}$=55.5 Hz), 1.85 (s, CH$_3$) ppm.

$^{19}$F NMR (376 MHz, CDCl$_3$; CFCl$_3$) [Z/E signal ratio 27:73]. δ=58.41 (s, OCF$_3$), −58.46 (s, OCF$_3$), −121.90 (d, CHF$_2$, $^2J_{F-H}$=55.4 Hz), −121.95 (d, CHF$_2$, $^2J_{F-H}$=55.4 Hz) ppm.

$^{13}$C NMR (101 MHz, CDCl$_3$; Me$_4$Si) δ=166.44 (t, CCHF$_2$, $^2J_{C-F}$=29.1 Hz), 141.52 (s, COCF$_3$), 138.31 (s, 1-C$_{arom}$), 127.75 (s, 4-C$_{arom}$), 125.82 (s, 5-C$_{arom}$), 122.38 (s, 6-C$_{arom}$), 122.14 (q, OCF$_3$, $^1J_{C-F}$=234.3 Hz), 120.96 (s, 3-C$_{arom}$), 114.62 (t, CHF$_2$, $^1J_{C-F}$=242.9 Hz), 12.96 (s, CH$_3$) ppm.

HRMS (ESI positive) for C$_{10}$H$_9$F$_5$NO [M+H]: calcd 254.0599; found 254.0622.

EXAMPLE 22

N-(1,1-Difluoropropan-2-ylidene)-3-(trifluoromethoxy)aniline (II-22)

Under argon atmosphere, an excess of cold 1,1-difluoroacetone (2 eq., 1.06 g, 0.92 mL, 11.3 mmol) was added to 3-(trifluoromethoxy)aniline (IV-9) (1 eq., 1 g, 0.76 mL, 5.65 mmol) in anhydrous dichloromethane (11 mL) in presence of molecular sieves (MS) 4 Å. Then the reaction mixture was stirred for 7 h at room temperature. MS was then filtered off on celite and washed with ether. The filtrate was concentrated under reduce pressure to give the product (II-22) as a brown oil in 93% yield (1.32 g). The compound was used without any further purification.

$^1$H NMR (400 MHz, CDCl$_3$; Me$_4$Si) δ=7.37 (t, 5-CH$_{arom}$, $^3J_{H-H}$=8.1 Hz), 7.04-6.99 (m, 4-CH$_{arom}$), 6.69 (d, 6-CH$_{arom}$, $^3J_{H-H}$=7.9 Hz), 6.66 (s, 2-CH$_{arom}$), 6.03 (t, CHF$_2$, $^2J_{H-F}$=55.5 Hz), 1.94 (s, CH$_3$) ppm.

$^{19}$F NMR (376 MHz, CDCl$_3$; CFCl$_3$) δ=−58.10 (s, OCF$_3$), −121.65 (d, CHF$_2$, $^2J_{F-H}$=55.6 Hz).

$^{13}$C NMR (101 MHz, CDCl$_3$; Me$_4$Si) δ=164.80 (t, CCHF$_2$, $_2J_{C-F}$=29.0 Hz), 150.07-150.02 (m, 1-C$_{arom}$+COCF$_3$), 130.57 (s, 5-C$_{arom}$), 121.72 (q, OCF$_3$, $^1J_{C-F}$=258.6 Hz), 117.37 (s, 4-C$_{arom}$), 117.00 (s, 6-C$_{arom}$), 114.68 (t, CHF$_2$, $^1J_{C-F}$=243.2 Hz), 111.92 (s, 2-C$_{arom}$), 12.74 (s, CH$_3$) ppm.

HRMS (ESI positive) for C$_{10}$H$_9$F$_5$NO [M+H]: calcd 254.0599; found 254.0583.

EXAMPLE 23

N-(1,1-Difluoropropan-2-ylidene)-4-(trifluoromethoxy)aniline (II-23)

Under argon atmosphere, an excess of cold 1,1-difluoroacetone (2 eq., 2.12 g, 1.83 mL, 22.6 mmol) was added to 4-(trifluoromethoxy)aniline (IV-10) (1 eq., 2 g, 1.53 mL, 11.3 mmol) in anhydrous dichloromethane (23 mL) in presence of molecular sieves (MS) 4 Å. Then the reaction mixture was stirred for 3 h at room temperature. MS was then filtered off on celite and washed with ether. The filtrate was concentrated under reduce pressure to give the product (II-23) as a brown oil in 91% yield (2.59 g). The compound was used without any further purification.

$^1$H NMR (400 MHz, CDCl$_3$; Me$_4$Si) δ=7.22 (d, 2,6-CH$_{arom}$, $^3J_{H-H}$=8.6 Hz), 6.78 (d, 3,5-CH$_{arom}$, $^3J_{H-H}$=8.8 Hz), 6.03 (t, CHF$_2$, $^2J_{H-F}$=55.6 Hz), 1.94 (s, CH$_3$) ppm.

$^{19}$F NMR (376 MHz, CDCl$_3$; CFCl$_3$) δ=−58.44 (s, OCF$_3$), −121.67 (dd, CHF$_2$, $^2J_{F-H}$=55.6, $^4J_{F-H}$=2 Hz) ppm.

$^{13}$C NMR (101 MHz, CDCl$_3$; Me$_4$Si) δ=164.54 (t, CCHF$_2$, $^2J_{C-F}$=28.9 Hz), 147.21 (s, 1-C$_{arom}$), 146.39 (d, COCF$_3$, $^3J_{C-F}$=2 Hz), 122.10 (s, 2,6-C$_{arom}$), 120.76 (q, OCF$_3$, $^1J_{C-F}$=256.7 Hz), 120.34 (s, 3,5-C$_{arom}$), 114.84 (t, CHF$_2$, $^1J_{C-F}$=244.4 Hz), 12.38 (s, CH$_3$) ppm.

HRMS (ESI positive) for $C_{10}H_9F_5NO$ [M+H]: calcd 254.0599; found 254.0622.

EXAMPLE 24

3-N-(1,1-Difluoropropan-2-ylidene)-1-N,N-dimethylbenzene-1,3-diamine (II-24)

Under argon atmosphere, an excess of cold 1,1-difluoroacetone (2 eq., 959 mg, 0.83 mL, 10.2 mmol) was added to 1-N,N-dimethyl-1,3-phenylenediamine dihydrochloride (1 eq., 695 mg, 5.1 mmol) and sodium hydride (2.1 eq., 257.2 mg, 10.72 mmol) in anhydrous dichloromethane (15 mL) in presence of molecular sieves (MS) 4 Å. Then the reaction mixture was stirred for 24 h at room temperature. MS was then filtered off on celite and washed with ether. The filtrate was concentrated under reduce pressure to give the product (II-24) as a black paste (1.26 g) in mixture with starting material and impurities. The compound was used without any further purification.

$^1$H NMR (400 MHz, CDCl$_3$; Me$_4$Si) δ=7.21 (t, 5-CH$_{arom}$, $^3J_{H-H}$=8.2 Hz), 6.56-6.51 (m, 4-CH$_{arom}$), 6.13-6.08 (m, 2,6-CH$_{arom}$), 6.06 (t, CHF$_2$, $^2J_{H-F}$=55.5 Hz), 2.95 (s, N(CH$_3$)$_2$), 1.96 (s, CH$_3$) ppm.

$^{19}$F NMR (376 MHz, CDCl$_3$; CFCl$_3$) δ=−121.31 (d, CHF$_2$, $^2J_{F-H}$=55.5 Hz) ppm.

HRMS (ESI positive) for $C_{11}H_{15}F_2N_2$ [M+H]: calcd 213.1198; found 213.1209.

EXAMPLE 25

4-N-(1,1-Difluoropropan-2-ylidene)-1-N,N-dimethylbenzene-1,4-diamine (II-25)

Under argon atmosphere, an excess of cold 1,1-difluoroacetone (2 eq., 1.38 g, 1.19 mL, 14.7 mmol) was added to N,N-dimethyl-1,4-benzenediamine (IV-11) (1 eq., 1 g, 0.92 mL, 7.35 mmol) in anhydrous dichloromethane (15 mL) in presence of molecular sieves (MS) 4 Å. Then the reaction mixture was stirred for 20 h at room temperature. MS was then filtered off on celite and washed with ether. The filtrate was concentrated under reduce pressure to give the product (II-25) as a yellow solid in 94% yield (1.46 g). The compound was used without any further purification.

$^1$H NMR (400 MHz, CDCl$_3$; Me$_4$Si) δ=6.77 (A$_2$B$_2$, 2,6-CH$_{arom}$+3,5-CH$_{arom}$, $^3J_{H-H}$=8.9 Hz, Δv=27.76 Hz), 6.05 (t, CHF$_2$, $^2J_{H-F}$=55.9 Hz), 2.96 (s, N(CH$_3$)$_2$), 2.03 (s, CH$_3$) ppm.

$^{19}$F NMR (376 MHz, CDCl$_3$; CFCl$_3$) δ=−120.62 (d, CHF$_2$, $^2J_{F-H}$=55.9 Hz) ppm.

$^{13}$C NMR (101 MHz, CDCl$_3$; Me$_4$Si) δ=161.26 (t, CCHF$_2$, $^2J_{C-F}$=28.4 Hz), 148.61 (s, CN(CH$_3$)$_2$), 137.60 (s, 1-C$_{arom}$), 121.72 (s, 2,6-C$_{arom}$), 115.70 (t, CHF$_2$, $^1J_{C-F}$=242.6 Hz), 112.84 (s, 3,5-C$_{arom}$), 40.83 (s, N(CH$_3$)$_2$), 12.74 (s, CH$_3$) ppm.

HRMS (ESI positive) for $C_{11}H_{15}F_2N_2$ [M+H]: calcd 213.1198, found 213.1214.

$C_{11}H_{14}F_2N_2$ (212): calcd (%) N, 13.19; C, 62.19; H, 6.60; found N, 13.22; C, 61.99; H, 6.68.

MP: 80.5-82° C.

EXAMPLE 26

N-(1,1-Difluoropropan-2-ylidene)-3-fluoro-2-methylaniline (II-26)

Under argon atmosphere, an excess of cold 1,1-difluoroacetone (2 eq., 3.01 g, 2.59 mL, 32 mmol) was added to 3-fluoro-2-methylaniline (IV-12) (1 eq., 2 g, 1.82 mL, 16 mmol) in anhydrous dichloromethane (30 mL) in presence of molecular sieves (MS) 4 Å. Then the reaction mixture was stirred for 18 h at room temperature. MS was then filtered off on celite and washed with ether. The filtrate was concentrated under reduce pressure to give the product (II-26) as a brown oil in 90% yield (2.88 g). The compound was used without any further purification.

$^1$H NMR (400 MHz, CDCl$_3$; Me$_4$Si) δ=7.16-7.13 (m, 4-CH$_{arom}$), 6.83 (t, 5-CH$_{arom}$, $^3J_{H-H}$=8.8 Hz), 6.41 (d, 6-CH$_{arom}$, $^3J_{H-H}$=7.9 Hz), 6.10 (t, CHF$_2$, $^2J_{H-F}$=55.5 Hz), 1.99 (d, C$_{arom}$CH$_3$, $^4J_{H-F}$=2.0 Hz), 1.89 (s, CH$_3$) ppm.

$^{19}$F NMR (376 MHz, CDCl$_3$; CFCl$_3$) δ=−116.18−−116.24 (m, F), −121.21 (dd, CHF$_2$, $^2J_{F-H}$=55.5, $^4J_{F-H}$=2.4 Hz) ppm.

$^{13}$C NMR (101 MHz, CDCl$_3$; Me$_4$Si) δ=164.50 (t, CCHF$_2$, $^2J_{C-F}$=29.0 Hz), 161.79 (d, CF, $^1J_{C-F}$=244.3 Hz), 148.91 (d, 1-C$_{arom}$, $^3J_{C-F}$=7.8 Hz), 126.98 (d, 4-C$_{arom}$, $^2J_{C-F}$=9.8 Hz), 114.68 (s, 2-C$_{arom}$), 114.55 (t, CHF$_2$, $^1J_{C-F}$=243.0 Hz), 113.50 (d, 6-C$_{arom}$, $^4J_{C-F}$=3.1 Hz), 111.17 (d, 5-C$_{arom}$, $^3J_{C-F}$=23.0 Hz), 12.83 (s, CH$_3$), 9.02 (d, C$_{arom}$CH$_3$, $^3J_{C-F}$=4.8 Hz) ppm.

HRMS (ESI positive) for $C_{10}H_{11}F_3N$ [M+H]: calcd 202.0838; found 202.0866.

EXAMPLE 27

3-Chloro-N-(1,1-difluoropropan-2-ylidene)-2-methylaniline (II-27)

Under argon atmosphere, an excess of cold 1,1-difluoroacetone (2 eq., 2.66 g, 2.29 mL, 28.2 mmol) was added to 3-chloro-2-methylaniline (IV-13) (1 eq., 2 g, 1.71 mL, 14.1 mmol) in anhydrous dichloromethane (30 mL) in presence of molecular sieves (MS) 4 Å. Then the reaction mixture was stirred for 18 h at room temperature. MS was then filtered off on celite and washed with ether. The filtrate was concentrated under reduce pressure to give the product (II-27) as a brown oil in 91% yield (2.79 g). The compound was used without any further purification.

$^1$H NMR (400 MHz, CDCl$_3$; Me$_4$Si) δ=7.17 (dd, 4-CH$_{arom}$, $^3J_{H-H}$=8.0, $^4J_{H-H}$=1.1 Hz), 7.10 (t, 5-CH$_{arom}$, $^3J_{H-H}$=7.7 Hz), 6.52 (dd, 6-CH$_{arom}$, $^3J_{H-H}$=7.7, $^4J_{H-H}$=0.9 Hz), 6.11 (t, CHF$_2$, $^2J_{H-F}$=55.5 Hz), 2.12 (s, C$_{arom}$CH$_3$), 1.88 (s, CH$_3$) ppm.

$^{19}$F NMR (376 MHz, CDCl$_3$; CFCl$_3$) δ=−121.15 (d, CHF$_2$, $^2J_{F-H}$=55.5 Hz) ppm.

$^{13}$C NMR (101 MHz, CDCl$_3$; Me$_4$Si) δ=164.43 (t, CCHF$_2$, $^2J_{C-F}$=28.9 Hz), 148.44 (s, 1-C$_{arom}$), 135.57 (s, CCl), 127.06 (s, 5-C$_{arom}$), 125.48 (s, 4-C$_{arom}$), 116.39 (s, 6-C$_{arom}$), 114.63 (t, CHF$_2$, $^1J_{C-F}$=243.1 Hz), 113.56 (S, 2-C$_{arom}$), 14.26 (s, C$_{arom}$CH$_3$), 12.89 (s, CH$_3$) ppm.

HRMS (ESI positive) for $C_{10}H_{11}F_2NCl$ [M+H]: calcd 218.0543; found 218.0557.

EXAMPLE 28

N-(1,1-Difluoropropan-2-ylidene)pyridin-3-amine (II-28)

Under argon atmosphere, an excess of cold 1,1-difluoroacetone (2 eq., 2 g, 1.72 mL, 21.3 mmol) was added to 3-aminopyridine (1 eq., 1 g, 10.6 mmol) in anhydrous dichloromethane (20 mL) in presence of molecular sieves (MS) 4 Å. Then the reaction mixture was stirred for 25 h at room temperature. MS was then filtered off on celite and washed with ether. The filtrate was concentrated under reduce pressure to give the product (II-28) as a brown oil in 79% yield (1.42 g) in mixture with compound from ketone auto-condensation. The compound was used without any further purification.

$^1$H NMR (400 MHz, CDCl$_3$; Me$_4$Si) δ=8.42-8.34 (m, 6-CH$_{arom}$), 8.08 (s, 2-CH$_{arom}$), 7.34-7.30 (m, 4-CH$_{arom}$), 7.15-7.12 (m, 5-CH$_{arom}$), 6.04 (t, CHF$_2$, $^2J_{H-F}$=55.4 Hz), 1.95 (s, CH$_3$) ppm.
$^{19}$F NMR (376 MHz, CDCl$_3$; CFCl$_3$) δ=−121.26−−121.61 (m, CHF$_2$) ppm.
$^{13}$C NMR (101 MHz, CDCl$_3$; Me$_4$Si) δ=165.62 (t, CCHF$_2$, $^2J_{C-F}$=29.1 Hz), 146.10 (s, 6-C$_{arom}$), 144.48 (s, 3-C$_{arom}$), 140.17 (s, 2-C$_{arom}$), 126.98 (s, 5-C$_{arom}$), 123.94 (s, 4-C$_{arom}$), 114.42 (t, CHF$_2$, $^1J_{C-F}$=243.5 Hz), 13.03 (s, CH$_3$) ppm.
HRMS (ESI positive) for C$_8$H$_9$F$_2$N$_2$ [M+H]: calcd 171.0728; found 171.0726.

EXAMPLE 29

3-Chloro-N-(1,1-difluoropropan-2-ylidene)aniline (II-29)

Under argon atmosphere, an excess of cold 1,1-difluoroacetone (2 eq., 5.9 g, 5.08 mL, 62.7 mmol) was added to 3-chloroaniline (IV-14) (1 eq., 4 g, 3.33 mL, 31.4 mmol) in anhydrous dichloromethane (59 mL) in presence of molecular sieves (MS) 4 Å. Then the reaction mixture was stirred for 18 h at room temperature. MS was then filtered off on celite and washed with ether. The filtrate was concentrated under reduce pressure to give the product (II-29) as a brown oil (9.68 g) in mixture with compound from ketone auto-condensation and impurities. The compound was used without any further purification.

$^1$H NMR (400 MHz, CDCl$_3$; Me$_4$Si) δ=7.31 (t, 5-CH$_{arom}$, $^3J_{H-H}$=8.0 Hz), 7.16 (d, 4-CH$_{arom}$, $^3J_{H-H}$=8.1 Hz), 6.81 (t, 2-CH$_{arom}$, $^4J_{H-H}$=1.9 Hz), 6.68 (d, 6-CH$_{arom}$, $^3J_{H-H}$=7.9 Hz), 6.06 (t, CHF$_2$, $^2J_{H-F}$=55.4 Hz), 1.97 (s, CH$_3$) ppm.
$^{19}$F NMR (376 MHz, CDCl$_3$; CFCl$_3$) δ=−121.46 (d, CHF$_2$, $^2J_{F-H}$=55.4 Hz) ppm.
$^{13}$C NMR (101 MHz, CDCl$_3$; Me$_4$Si) δ=164.76 (t, CCHF$_2$, $^2J_{C-F}$=29.0 Hz), 149.64 (s, 1-C$_{arom}$), 134.99 (s, CCl), 130.44 (s, 5-C$_{arom}$), 124.96 (s, 4-C$_{arom}$), 119.18 (s, 2-C$_{arom}$), 117.24 (s, 6-C$_{arom}$), 114.55 (t, CHF$_2$, $^1J_{C-F}$=243.2 Hz), 12.87 (s, CH$_3$) ppm.
HRMS (ESI positive) for C$_9$H$_9$F$_2$NCl [M+H]: calcd 204.0386; found 204.0367.

EXAMPLE 30

N-(1,1-Difluoropropan-2-ylidene)-3-(trifluoromethyl)aniline (II-30)

Under argon atmosphere, an excess of cold 1,1-difluoroacetone (2 eq., 1.17 g, 1.01 mL, 12.4 mmol) was added to 3-(trifluoromethyl)aniline (IV-15) (1 eq., 1 g, 0.767 mL, 6.21 mmol) in anhydrous dichloromethane (12 mL) in presence of molecular sieves (MS) 4 Å. Then the reaction mixture was stirred for 5 h at room temperature. MS was then filtered off on celite and washed with ether. The filtrate was concentrated under reduce pressure to give the product (II-30) as a brown oil in 93% yield (1.47 g) in mixture with compound from ketone auto-condensation. The compound was used without any further purification.

$^1$H NMR (400 MHz, CDCl$_3$; Me$_4$Si) δ=7.49 (t, 5-CH$_{arom}$, $^3J_{H-H}$=7.8 Hz), 7.42 (d, 4-CH$_{arom}$, $^3J_{H-H}$=7.8 Hz), 7.03 (s, 2-CH$_{arom}$), 6.94 (d, 4-CH$_{arom}$, $^3J_{H-H}$=7.2 Hz), 6.05 (t, CHF$_2$, $^2J_{H-F}$=55.5 Hz), 1.95 (s, CH$_3$) ppm.
$^{19}$F NMR (376 MHz, CDCl$_3$; CFCl$_3$) δ=−62.80 (s, CF$_3$), −121.44 (d, CHF$_2$, $^2J_{F-H}$=55.4 Hz) ppm.
$^{13}$C NMR (101 MHz, CDCl$_3$; Me$_4$Si) δ=165.21 (t, CCHF$_2$, $^2J_{C-F}$=28.9 Hz), 148.91 (s, 1-C$_{arom}$), 131.84 (q, 3-C$_{arom}$, $^2J_{C-F}$=32.5 Hz), 129.96 (s, 5-C$_{arom}$), 124.03 (q, CF$_3$, $^1J_{C-F}$=272.3 Hz), 122.38 (s, 6-C$_{arom}$), 121.68 (q, 4-C$_{arom}$, $^3J_{C-F}$=3.8 Hz), 116.01 (q, 2-C$_{arom}$, $^3J_{C-F}$=4.0 Hz), 114.53 (t, CHF$_2$, $^1J_{C-F}$=243.2 Hz), 12.78 (s, CH$_3$) ppm.
HRMS (ESI positive) for C$_{10}$H$_9$F$_5$N [M+H]: calcd 238.0650; found 238.0660.

EXAMPLE 31

N-(1,1-Difluoropropan-2-ylidene)-4-(trifluoromethyl)aniline (II-31)

Under argon atmosphere, an excess of cold 1,1-difluoroacetone (2 eq., 583 mg, 0.503 mL, 6.21 mmol) was added to 4-(trifluoromethyl)aniline (IV-16) (1 eq., 500 mg, 0.386 mL, 3.1 mmol) in anhydrous dichloromethane (6 mL) in presence of anhydrous magnesium sulphate (MgSO$_4$). Then the reaction mixture was stirred for 16 h at room temperature. MgSO$_4$ was then filtered off on celite and washed with ether. The filtrate was concentrated under reduce pressure to give the product (II-31) as a brown oil 29% yield (212 mg) in mixture with starting material (72% of conversion). The compound was used without any further purification.

$^1$H NMR (400 MHz, CDCl$_3$; Me$_4$Si) δ=7.63 (d, 3,5-CH$_{arom}$, $^3J_{H-H}$=8.3 Hz), 6.85 (d, 2,6-CH$_{arom}$, $^3J_{H-H}$=8.2 Hz), 6.05 (t, CHF$_2$, $^2J_{H-F}$=55.4 Hz), 1.93 (s, CH$_3$) ppm.
$^{19}$F NMR (376 MHz, CDCl$_3$; CFCl$_3$) δ=−62.13 (s, CF$_3$), −121.34−−121.59 (m, CHF$_2$,) ppm.
$^{13}$C NMR (101 MHz, CDCl$_3$; Me$_4$Si) δ=164.59 (t, CCHF$_2$, $^2J_{C-F}$=29.0 Hz), 151.64 (s, 1-C$_{arom}$), 126.64 (q, 3,5-C$_{arom}$, $^3J_{C-F}$=3.8 Hz), 124.30 (q, CF$_3$, $^1J_{C-F}$=271.6 Hz), 120.30 (q, 4-C$_{arom}$, $^2J_{C-F}$=32.6 Hz), 119.03 (s, 2,6-C$_{arom}$), 114.49 (t, CHF$_2$, $^1J_{C-F}$=243.3 Hz), 12.97 (s, CH$_3$) ppm.
HRMS (ESI positive) for C$_{10}$H$_9$F$_5$N [M+H]: calcd 238.0650; found 238.0658.

EXAMPLE 32

N-(1,1-Difluoropropan-2-ylidene)-2-(trifluoromethyl)aniline (II-32)

Under argon atmosphere, an excess of cold 1,1-difluoroacetone (2 eq., 583 mg, 0.503 mL, 6.21 mmol) was added to 2-(trifluoromethyl)aniline (IV-17) (1 eq., 500 mg, 0.386 mL, 3.1 mmol) in anhydrous dichloromethane (6 mL) in presence of anhydrous magnesium sulphate (MgSO$_4$). Then the reaction mixture was stirred for 16 h at room temperature. MgSO$_4$ was then filtered off on celite and washed with ether. The filtrate was concentrated under reduce pressure to give the product (II-32) as a brown oil 40% yield (291.5 mg) in mixture with starting material (83% of conversion). The compound was used without any further purification.

$^1$H NMR (400 MHz, CDCl$_3$; Me$_4$Si) δ=7.67 (d, 3-CH$_{arom}$, $^3J_{H-H}$=7.9 Hz), 7.52 (t, 5-CH$_{arom}$, $^3J_{H-H}$=7.7 Hz), 7.23 (t, 4-CH$_{arom}$, $^3J_{H-H}$=7.7 Hz), 6.72 (d, 6-CH$_{arom}$, $^3J_{H-H}$=7.9 Hz), 6.08 (t, CHF$_2$, $^2J_{H-F}$=55.4 Hz), 1.90 (s, CH$_3$) ppm.
$^{19}$F NMR (376 MHz, CDCl$_3$; CFCl$_3$) δ=−61.85 (s, CF$_3$,), −121.82 (d, CHF$_2$, $^2J_{F-H}$=55.4 Hz) ppm.
$^{13}$C NMR (101 MHz, CDCl$_3$; Me$_4$Si) δ=165.58 (t, CCHF$_2$, $^2J_{C-F}$=29.4 Hz), 146.98 (q, 1-C$_{arom}$, $^3J_{C-F}$=2.02 Hz), 132.87 (s, 5-C$_{arom}$), 126.77 (q, 3-C$_{arom}$, $^3J_{C-F}$=5.05 Hz), 124.50 (s, 4-C$_{arom}$), 123.67 (q, CF$_3$, $^1J_{C-F}$=273.0 Hz), 119.65 (q, 2-C$_{arom}$, $^2J_{C-F}$=31.3 Hz), 119.18 (s, 6-C$_{arom}$), 114.27 (t, CHF$_2$, $^1J_{C-F}$=243.3 Hz), 13.42 (s, CH$_3$) ppm.
HRMS (ESI positive) for C$_{10}$H$_9$F$_5$N [M+H]: calcd 238.0650; found 238.0654.

EXAMPLE 33

N-(1,1-Difluoropropan-2-ylidene)-2-phenylaniline (II-33)

Under argon atmosphere, an excess of cold 1,1-difluoroacetone (2 eq., 562 mg, 0.485 mL, 5.98 mmol) was added to 2-aminodiphenyl (IV-18) (1 eq., 505 mg, 2.99 mmol) in anhydrous dichloromethane (6 mL) in presence of anhydrous magnesium sulphate (MgSO$_4$). Then the reaction mixture was stirred for 14 h at room temperature. MgSO$_4$ was then filtered off on celite and washed with ether. The filtrate was concentrated under reduce pressure to give the product (II-33) as a brown oil (953.7 mg) in mixture with unknown species. The compound was used without any further purification.

$^1$H NMR (400 MHz, CDCl$_3$; Me$_4$Si) δ=7.42-7.23 (m, 3,4,5,2',3',4',5',6'-CH$_{arom}$), 6.71 (dd, 6-CH$_{arom}$, $^3J_{H-H}$=7.8, $^4J_{H-H}$=1.0 Hz), 5.88 (t, CHF$_2$, $^2J_{H-F}$=55.6 Hz), 1.64 (s, CH$_3$) ppm.

$^{19}$F NMR (376 MHz, CDCl$_3$; CFCl$_3$) δ=−121.61 (d, CHF$_2$, $^2J_{F-H}$=55.5 Hz) ppm.

$^{13}$C NMR (101 MHz, CDCl$_3$; Me$_4$Si) δ=163.53 (t, CCHF$_2$, $^2J_{C-F}$=28.8 Hz), 146.07 (s, 1-C$_{arom}$), 139.00 (s, 1'-C$_{arom}$), 132.02 (s, 2-C$_{arom}$), 131.44-123.83 (m, 3,4,5,2', 3',4',5',6'-C$_{arom}$), 119.16 (s, 6-C$_{arom}$), 114.67 (t, CHF$_2$, $^1J_{C-F}$=243.2 Hz), 13.40 (s, CH$_3$) ppm.

HRMS (ESI positive) for C$_{15}$H$_{14}$F$_2$N [M+H]: calcd 246.1089; found 246.1112.

EXAMPLE 34

N-(1,1-Difluoropropan-2-ylidene)-2-(phenylsulfanyl)aniline (II-34)

Under argon atmosphere, an excess of cold 1,1-difluoroacetone (2 eq., 489 mg, 0.422 mL, 5.2 mmol) was added to 2-(phenylsulfanyl)aniline (IV-19) (1 eq., 523 mg, 2.6 mmol) in anhydrous dichloromethane (5 mL) in presence of anhydrous magnesium sulphate (MgSO$_4$). Then the reaction mixture was stirred for 12 h at room temperature. MgSO$_4$ was then filtered off on celite and washed with ether. The filtrate was concentrated under reduce pressure to give the product (II-34) as a brown oil (796.1 mg) in mixture with unknown species. The compound was used without any further purification.

$^1$H NMR (400 MHz, CDCl$_3$; Me$_4$Si) δ=7.34-7.20 (m, 3,2',3',4',5',6'-CH$_{arom}$), 7.09 (td, 4,5-CH$_{arom}$, $^3J_{H-H}$=7.65, $^4J_{H-H}$=1.3 Hz), 6.69 (dd, 6-CH$_{arom}$, $^3J_{H-H}$=7.8, $^4J_{H-H}$=1.1 Hz), 6.01 (t, CHF$_2$, $^2J_{H-F}$=55.5 Hz), 1.78 (s, CH$_3$) ppm.

$^{19}$F NMR (376 MHz, CDCl$_3$; CFCl$_3$) δ=−121.06 (d, CHF$_2$, $^2J_{F-H}$=55.4 Hz) ppm.

$^{13}$C NMR (101 MHz, CDCl$_3$; Me$_4$Si) δ=164.78 (t, CCHF$_2$, $^2J_{C-F}$=28.9 Hz), 148.85 (s, 1-C$_{arom}$), 136.88 (s, 1'-C$_{arom}$), 134.64 (s, 2-C$_{arom}$), 132.37-127.42 (m, 3,2',3',4', 5',6'-C$_{arom}$), 126.57 (s, 5-C$_{arom}$), 125.43 (s, 4-C$_{arom}$), 118.87 (s, 6-C$_{arom}$), 114.45 (t, CHF$_2$, $^1J_{C-F}$=243.3 Hz), 13.04 (s, CH$_3$) ppm.

HRMS (ESI positive) for C$_{15}$H$_{14}$F$_2$NS [M+H]: calcd 278.0810; found 278.0781.

EXAMPLE 35

5-[(1,1-Difluoropropan-2-ylidene)amino]-1-naphthol (II-35)

Under argon atmosphere, an excess of cold 1,1-difluoroacetone (2 eq., 590 mg, 0.509 mL, 6.28 mmol) was added to 5-amino-1-naphthol (1 eq., 500 mg, 3.14 mmol) in anhydrous dichloromethane (6 mL) in presence of anhydrous magnesium sulphate (MgSO$_4$). Then the reaction mixture was stirred for 14 h at room temperature. MgSO$_4$ was then filtered off on celite and washed with ether. The filtrate was concentrated under reduce pressure to give the product (II-35) as a purple solid in 91% yield (670 mg). The compound was used without any further purification.

$^1$H NMR (400 MHz, CDCl$_3$; Me$_4$Si) δ=8.01 (d, 8-CH$_{arom}$, $^3J_{H-H}$=8.5 Hz), 7.45 (t, 7-CH$_{arom}$, $^3J_{H-H}$=8.0 Hz), 7.35-7.17 (m, 3,4-CH$_{arom}$), 6.84 (d, 2-CH$_{arom}$, $^3J_{H-H}$=7.3 Hz), 6.78 (d, 6-CH$_{arom}$, $^3J_{H-H}$=7.2 Hz), 6.24 (t, CHF$_2$, $^2J_{H-F}$=55.6 Hz), 5.45 (s, OH), 1.91 (s, CH$_3$) ppm.

$^{19}$F NMR (376 MHz, CDCl$_3$; CFCl$_3$) δ=−120.84 (d, CHF$_2$, $^2J_{F-H}$=55.5 Hz) ppm.

$^{13}$C NMR (101 MHz, CDCl$_3$; Me$_4$Si) δ=165.18 (t, CCHF$_2$, $^2J_{C-F}$=28.9 Hz), 151.81 (s, 1-C$_{arom}$), 144.46 (s, 5-C$_{arom}$), 126.46 (s, C1-C—C8), 126.24 (s, 3-C$_{arom}$), 125.23 (s, C4-C—C5), 125.00 (s, 7-C$_{arom}$), 118.80 (s, 8-C$_{arom}$), 115.48 (s, 4-C$_{arom}$), 114.83 (t, CHF$_2$, $^1J_{C-F}$=243.3 Hz), 114.07 (s, 6-C$_{arom}$), 109.46 (s, 2-C$_{arom}$), 13.18 (s, CH$_3$) ppm.

HRMS (ESI positive) for C$_{13}$H$_{12}$F$_2$NO [M+H]: calcd 236.0881; found 236.0909.

EXAMPLE 36

4-(Difluoromethyl)-2-(trifluoromethyl)quinoline (I-1)

1,1,2,2-Tetrafluoro-N,N-dimethylethan-1-amine (TFEDMA) was activated by adding boron trifluoride diethyl etherate (1.2 eq., 511 mg, 0.46 mL, 3.61 mmol) in a solution of TFEDMA (1.2 eq., 523 mg, 0.42 mL, 3.61 mmol) in dry acetonitrile (5 mL) and stirred for 15 min. Then a solution of N-(1,1,1-trifluoropropan-2-ylidene)aniline (II-1) (1 eq., 562 mg, 3.01 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-1) as a yellow solid in 62% yield (458 mg).

$^1$H NMR (400 MHz, CDCl$_3$; Me$_4$Si) δ=8.33 (d, 8-CH$_{arom}$, $^3J_{H-H}$=8.5 Hz), 8.16 (d, 5-CH$_{arom}$, $^3J_{H-H}$=8.5 Hz), 7.93 (s, 3-CH$_{arom}$), 7.92-7.87 (m, 7-CH$_{arom}$), 7.80 (t, 6-CH$_{arom}$, $^3J_{H-H}$=7.7 Hz), 7.22 (t, 4-CHF$_2$, $^2J_{H-F}$=54.2 Hz) ppm.

$^{19}$F NMR (376 MHz, CDCl$_3$; CFCl$_3$) δ=−67.66 (s, CF$_3$), −115.53 (d, CHF$_2$, $^2J_{F-H}$=54.1 Hz) ppm.

$^{13}$C NMR (101 MHz, CDCl$_3$; Me$_4$Si) δ=147.94 (q, 2-C$_{arom}$, $^2J_{C-F}$=35.3 Hz), 147.87 (t, C8-C—N), 140.33 (t, 4-C$_{arom}$, $^2J_{C-F}$=22.3 Hz), 131.39 (s, 7-C$_{arom}$), 131.29 (s, 8-C$_{arom}$), 130.06 (s, 6-C$_{arom}$), 125.09 (s, C5-C—C4), 123.44 (s, 5-C$_{arom}$), 121.33 (q, 2-CCF$_3$, $^1J_{C-F}$=275.73 Hz), 114.14 (td, 3-C$_{arom}$, $^3J_{C-F}$=7.9, $^3J_{C-F}$=2.1 Hz), 112.74 (t, 4-CCHF$_2$, $^1J_{C-F}$=241.5 Hz) ppm.

HRMS (ESI positive) for C$_{11}$H$_7$F$_5$N [M+H]: calcd 248.0493, found 248.0520.

C$_{11}$H$_6$F$_5$N (247): calcd (%) N, 5.66; C, 53.40; H, 2.43; found N, 5.73; C, 53.83; H, 2.58.

MP: 64-65.1° C.

EXAMPLE 37

2,4-Bis(difluoromethyl)quinoline (I-2)

1,1,2,2-Tetrafluoro-N,N-dimethylethan-1-amine (TFEDMA) was activated by adding boron trifluoride diethyl etherate (1.2 eq., 518 mg, 0.463 mL, 3.65 mmol) in a solution of TFEDMA (1.2 eq., 530 mg, 0.427 mL, 3.65 mmol) in dry acetonitrile (5 mL) and stirred for 5 min. Then a solution of N-(1,1-difluoropropan-2-ylidene)aniline (II-14) (1 eq., 515 mg, 3.04 mmol) in dry acetonitrile (5 mL)

was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-2) as a yellow solid in 77% yield (537 mg).

$^1$H NMR (400 MHz, CDCl$_3$; Me$_4$Si) δ=8.23 (d, 8-CH$_{arom}$, $^3J_{H-H}$=8.5 Hz), 8.14 (d, 5-CH$_{arom}$, $^3J_{H-H}$=8.5 Hz), 7.92 (s, 3-CH$_{arom}$), 7.86 (t, 7-CH$_{arom}$, $^3J_{H-H}$=7.7 Hz), 7.74 (t, 6-CH$_{arom}$, $^3J_{H-H}$=7.7 Hz), 7.19 (t, 4-CCHF$_2$, $^2J_{H-F}$=54.3 Hz), 6.81 (t, 2-CCHF$_2$, $^2J_{H-F}$=55.1 Hz) ppm.

$^{19}$F NMR (376 MHz, CDCl$_3$; CFCl$_3$) δ=−114.46 (d, 2-CHF$_2$, $^2J_{F-H}$=55.1 Hz), −115.16 (d, 4-CHF$_2$, $^2J_{F-H}$=54.3 Hz) ppm.

$^{13}$C NMR (101 MHz, CDCl$_3$; Me$_4$Si) δ=152.70 (t, 2-C$_{arom}$, $^2J_{C-F}$=27.1 Hz), 147.80 (s, C8-C—N), 139.93 (t, 4-C$_{arom}$, $^2J_{C-F}$=22.2 Hz), 130.91 (s, 7-C$_{arom}$), 130.83 (s, 8-C$_{arom}$), 129.33 (s, 6-C$_{arom}$), 124.84 (s, C5-C—C4), 123.55 (s, 5-C$_{arom}$), 114.37 (t, 4-CCHF$_2$, $^1J_{C-F}$=242.0 Hz), 114.32-114.17 (m, 3-C$_{arom}$), 113.13 (t, 2-CCHF$_2$, $^1J_{C-F}$=241.2 Hz) ppm.

C$_{11}$H$_7$F$_4$N (229): calcd (%) N, 6.10; C, 57.60; H, 3.05; found N, 6.20; C, 57.56; H, 2.96.

MP: 48.2-49.7° C.

EXAMPLE 38

4-(Difluoromethyl)-8-methoxy-2-(trifluoromethyl)quinoline (I-3)

1,1,2,2-Tetrafluoro-N,N-dimethylethan-1-amine (TFEDMA) was activated by adding boron trifluoride diethyl etherate (1.2 eq., 400 mg, 0.357 mL, 2.82 mmol) in a solution of TFEDMA (1.2 eq., 408 mg, 0.33 mL, 2.82 mmol) in dry acetonitrile (5 mL) and stirred for 15 min. Then a solution of 2-methoxy-N-(1,1,1-trifluoropropan-2-ylidene)aniline (II-2) (1 eq., 510 mg, 2.35 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (10-25%) to provide the final compound (I-3) as a yellow solid in 88% yield (575 mg).

$^1$H NMR (400 MHz, CDCl$_3$; Me$_4$Si) δ=7.97 (s, 5-CH$_{arom}$), 7.74-7.63 (m, 6,7-CH$_{arom}$), 7.21 (d, 3-CH$_{arom}$, $^4J_{H-F}$=7.8 Hz), 7.20 (t, 4-CCHF$_2$, $^2J_{H-F}$=54.3 Hz), 4.12 (s, CH$_3$) ppm.

$^{19}$F NMR (376 MHz, CDCl$_3$; CFCl$_3$) δ=−67.16 (s, CF$_3$), −116.17 (d, 4-CHF$_2$, $^2J_{F-H}$=54.4 Hz) ppm.

$^{13}$C NMR (101 MHz, CDCl$_3$; Me$_4$Si) δ=156.58 (s, COCH$_3$), 146.50 (q, 2-C$_{arom}$, $^2J_{C-F}$=35.7 Hz), 140.11 (t, 4-C$_{arom}$, $^2J_{C-F}$=22.2 Hz), 139.95 (s, C8-C—N), 130.74 (s, 6-C$_{arom}$), 126.43 (s, C5-C—C4), 121.40 (q, 2-CCF$_3$, $^1J_{C-F}$=275.2 Hz), 114.70-114.16 (m, 5-C$_{arom}$+7-C$_{arom}$), 112.55 (t, 4-CCHF$_2$, $^1J_{C-F}$=241.5 Hz), 109.56 (s, 3-C$_{arom}$), 56.58 (s, CH$_3$) ppm.

C$_{12}$H$_8$F$_5$NO (277): calcd (%) N, 5.05; C, 51.95; H, 2.88; found N, 5.16; C, 51.92; H, 2.74.

MP: 72.5-76.8° C.

EXAMPLE 39

2,4-Bis(difluoromethyl)-8-methoxyquinoline (I-4)

1,1,2,2-Tetrafluoro-N,N-dimethylethan-1-amine (TFEDMA) was activated by adding boron trifluoride diethyl etherate (1.2 eq., 429 mg, 0.383 mL, 3.02 mmol) in a solution of TFEDMA (1.2 eq., 438 mg, 0.354 mL, 3.02 mmol) in dry acetonitrile (5 mL) and stirred for 15 min. Then a solution of N-(1,1-difluoropropan-2-ylidene)-2-methoxyaniline (II-15) (1 eq., 502 mg, 2.52 mmol) in dry acetonitrile (5mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (10-25%) to provide the final compound (I-4) as a brown solid in 72% yield (473 mg).

$^1$H NMR (400 MHz, CDCl$_3$; Me$_4$Si) δ=7.94 (s, 5-CH$_{arom}$), 7.62 (d, 6,7-CH$_{arom}$, $^3J_{H-H}$=4.2 Hz), 7.31-7.02 (m, 3-CH$_{arom}$+4-CCHF$_2$), 6.88 (t, 2-CCHF$_2$, $^2J_{H-F}$=51.4 Hz), 4.09 (s, CH$_3$) ppm.

$^{19}$F NMR (376 MHz, CDCl$_3$; CFCl$_3$) δ=−113.42 (d, 2-CHF$_2$, $^2J_{F-H}$=54.9 Hz), −115.88 (d, 4-CHF$_2$, $^2J_{F-H}$=54.3 Hz) ppm.

$^{13}$C NMR (101 MHz, CDCl$_3$; Me$_4$Si) δ=156.17 (s, COCH$_3$), 151.14 (t, 2-C$_{arom}$, $^2J_{C-F}$=27.7 Hz), 140.04-139.19 (m, 4-C$_{arom}$+C8-C—N), 129.84 (s, 6-C$_{arom}$), 126.13 (s, C5-C—C4), 114.92 (s, 5-C$_{arom}$), 114.72 (t, 7-C$_{arom}$, J=7.9 Hz), 114.48 (t, 2-CCHF$_2$, $^1J_{C-F}$=241.9 Hz), 112.85 (t, 4-CCHF$_2$, $^1J_{C-F}$=241.1 Hz), 109.17 (s, 3-C$_{arom}$), 56.41 (s, CH$_3$) ppm.

C$_{12}$H$_9$F$_4$NO (259): calcd (%) N, 5.40; C, 55.55; H, 3.47; found N, 5.35; C, 55.30; H, 3.51.

MP: 96.8-98.6° C.

EXAMPLE 40

4-(Difluoromethyl)-7-methoxy-2-(trifluoromethyl)quinoline (I-5)

1,1,2,2-Tetrafluoro-N,N-dimethylethan-1-amine (TFEDMA) was activated by adding boron trifluoride diethyl etherate (1.2 eq., 392 mg, 0.35 mL, 2.77 mmol) in a solution of TFEDMA (1.2 eq., 401 mg, 0.324 mL, 2.77 mmol) in dry acetonitrile (5 mL) and stirred for 15 min. Then a solution of 3-methoxy-N-(1,1,1-trifluoropropan-2-ylidene)aniline (II-3) (1 eq., 500 mg, 2.3 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (10-25%) to provide the final compound (I-5) as a light brown solid in 64% yield (407 mg).

$^1$H NMR (400 MHz, CDCl$_3$; Me$_4$Si) δ=8.00 (d, 5-CH$_{arom}$, $^3J_{H-H}$=9.3 Hz), 7.76 (s, 3-CH$_{arom}$), 7.57 (d, 8-CH$_{arom}$, $^4J_{H-H}$=2.6 Hz), 7.39 (dd, 6-CH$_{arom}$, $^3J_{H-H}$=9.3, $^4J_{H-H}$=2.6 Hz), 7.14 (t, 4-CCHF$_2$, $^2J_{H-F}$=54.3 Hz), 3.97 (s, CH$_3$) ppm.

$^{19}$F NMR (376 MHz, CDCl$_3$; CFCl$_3$) δ=−67.74 (s, CF$_3$), −115.04 (d, 4-CHF$_2$, $^2J_{F-H}$=54.4 Hz) ppm.

$^{13}$C NMR (101 MHz, CDCl$_3$; Me$_4$Si) δ=161.92 (s, COCH$_3$), 150.09 (s, C8-C—N), 148.04 (q, 2-C$_{arom}$, $^2J_{C-F}$=35.2 Hz), 140.01 (t, 4-C$_{arom}$, $^2J_{C-F}$=22.4 Hz), 124.36 (s, 5-C$_{arom}$), 123.61 (s, 6-C$_{arom}$), 121.26 (q, 2-CCF$_3$, $^1J_{C-F}$=275.2 Hz), 120.32 (t, C5-C—C4, $^3J_{C-F}$=2.8 Hz), 112.86 (t, 4-CCHF$_2$, $^1J_{C-F}$=241.4 Hz), 111.81 (td, 3-C$_{arom}$, $^3J_{C-F}$=8.0, $^3J_{C-F}$=2.3 Hz), 108.56 (s, 8-C$_{arom}$), 55.91 (s, CH$_3$) ppm.

C$_{12}$H$_8$F$_5$NO (277): calcd (%) N, 5.05; C, 51.95; H, 2.88; found N, 5.14; C, 51.71; H, 2.87.

MP: 83.4-87.2° C.

EXAMPLE 41

2,4-Bis(difluoromethyl)-7-methoxyquinoline (I-6)

1,1,2,2-Tetrafluoro-N,N-dimethylethan-1-amine (TFEDMA) was activated by adding boron trifluoride diethyl etherate (1.2 eq., 431 mg, 0.386 mL, 3.04 mmol) in a solution of TFEDMA (1.2 eq., 441 mg, 0.356 mL, 3.04 mmol) in dry acetonitrile (5 mL) and stirred for 15 min. Then a solution of N-(1,1-difluoropropan-2-ylidene)-3-methoxyaniline (II-16) (1 eq., 505 mg, 2.54 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (10-25%) to provide the final compound (I-6) as a yellow solid in 78% yield (515 mg).

$^1$H NMR (400 MHz, CDCl$_3$; Me$_4$Si) δ=7.79 (d, 5-CH$_{arom}$, $^3J_{H-H}$=9.3 Hz), 7.57 (s, 3-CH$_{arom}$), 7.30 (d, 8-CH$_{arom}$, $^4J_{H-H}$=2.6 Hz), 7.14 (dd, 6-CH$_{arom}$, $^3J_{H-H}$=9.3, $^4J_{H-H}$=2.6 Hz), 6.94 (t, 4-CCHF$_2$, $^2J_{H-F}$=54.4 Hz), 6.62 (t, 2-CCHF$_2$, $^2J_{H-F}$=55.2 Hz), 3.79 (s, CH$_3$) ppm.

$^{19}$F NMR (376 MHz, CDCl$_3$; CFCl$_3$) δ=−114.79 (d, 2-CHF$_2$, $^2J_{F-H}$=54.4 Hz), −114.95 (d, 4-CHF$_2$, $^2J_{F-H}$=55.3 Hz) ppm.

$^{13}$C NMR (101 MHz, CDCl$_3$; Me$_4$Si) δ=161.45 (s, COCH$_3$), 152.86 (t, 2-C$_{arom}$, $^2J_{C-F}$=26.7 Hz), 149.83 (s, C8-C—N), 139.56 (t, 4-C$_{arom}$, $^2J_{C-F}$=22.2 Hz), 124.33 (s, 5-C$_{arom}$), 122.45 (s, 6-C$_{arom}$), 119.77 (t, C5-C—C4, $^3J_{C-F}$=2.8 Hz), 114.25 (t, 2-CCHF$_2$, $^1J_{C-F}$=242.4 Hz), 113.18 (t, 4-CCHF$_2$, $^1J_{C-F}$=241.0 Hz), 111.89-111.70 (m, 3-C$_{arom}$), 108.24 (s, 8-C$_{arom}$), 55.60 (s, CH$_3$) ppm.

C$_{12}$H$_9$F$_4$NO (259): calcd (%) N, 5.40; C, 55.55; H, 3.47; found N, 5.55; C, 55.57; H, 3.67.

MP: 55.4-56.9° C.

EXAMPLE 42

4-(Difluoromethyl)-6-methoxy-2-(trifluoromethyl)quinoline (I-7)

1,1,2,2-Tetrafluoro-N,N-dimethylethan-1-amine (TFEDMA) was activated by adding boron trifluoride diethyl etherate (1.2 eq., 394 mg, 0.352 mL, 2.78 mmol) in a solution of TFEDMA (1.2 eq., 402 mg, 0.325 mL, 2.78 mmol) in dry acetonitrile (5 mL) and stirred for 15 min. Then a solution of 4-methoxy-N-(1,1,1-trifluoropropan-2-ylidene)aniline (II-4) (1 eq., 502 mg, 2.31 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (10-25%) to provide the final compound (I-7) as a brown solid in 85% yield (543 mg).

$^1$H NMR (400 MHz, CDCl$_3$; Me$_4$Si) δ=8.16 (d, 8-CH$_{arom}$, $^3J_{H-H}$=9.3 Hz), 7.85 (s, 3-CH$_{arom}$), 7.50 (dd, 7-CH$_{arom}$, $^3J_{H-H}$=9.3, $^4J_{H-H}$=2.6 Hz), 7.29 (s, 5-CH$_{arom}$), 7.11 (t, 4-CCHF$_2$, $^2J_{H-F}$=54.3 Hz), 3.97 (s, CH$_3$) ppm.

$^{19}$F NMR (376 MHz, CDCl$_3$; CFCl$_3$) δ=−67.30 (s, CF$_3$), −115.95 (d, 4-CHF$_2$, $^2J_{F-H}$=54.4 Hz) ppm.

$^{13}$C NMR (101 MHz, CDCl$_3$; Me$_4$Si) δ=160.35 (s, COCH$_3$), 144.95 (q, 2-C$_{arom}$, $^2J_{C-F}$=35.4 Hz), 144.11 (s, C8-C—N), 138.21 (t, 4-C$_{arom}$, $^2J_{C-F}$=22.1 Hz), 132.56 (s, 8-C$_{arom}$), 126.63 (s, C5-C—C4), 124.40 (s, 7-C$_{arom}$), 121.43 (q, 2-CCF$_3$, $^1J_{C-F}$=274.7 Hz), 114.59 (td, 3-C$_{arom}$, $^3J_{C-F}$=8.1, $^3J_{C-F}$=2.3 Hz), 113.17 (t, 4-CCHF$_2$, $^1J_{C-F}$=241.1 Hz), 101.06 (s, 5-C$_{arom}$), 55.88 (s, CH$_3$) ppm.

C$_{12}$H$_8$F$_5$NO (277): calcd (%) N, 5.05; C, 51.95; H, 2.88; found N, 5.03; C, 51.64; H, 2.80.

MP: 105.9-108.2° C.

EXAMPLE 43

2,4-Bis(difluoromethyl)-6-methoxyquinoline (I-8)

1,1,2,2-Tetrafluoro-N,N-dimethylethan-1-amine (TFEDMA) was activated by adding boron trifluoride diethyl etherate (1.2 eq., 432 mg, 0.386 mL, 3.05 mmol) in a solution of TFEDMA (1.2 eq., 442 mg, 0.357 mL, 3.05 mmol) in dry acetonitrile (5 mL) and stirred for 15 min. Then a solution of N-(1,1-difluoropropan-2-ylidene)-4-methoxyaniline (II-17) (1 eq., 506 mg, 2.54 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (10-25%) to provide the final compound (I-8) as an orange solid in 71% yield (468 mg).

$^1$H NMR (400 MHz, CDCl$_3$; Me$_4$Si) δ=8.15 (d, 8-CH$_{arom}$, $^3J_{H-H}$=9.3 Hz), 7.90 (s, 3-CH$_{arom}$), 7.53 (dd, 7-CH$_{arom}$, $^3J_{H-H}$=9.3, $^4J_{H-H}$=2.5 Hz), 7.36 (s, 5-CH$_{arom}$), 7.16 (t, 4-CCHF$_2$, $^2J_{H-F}$=54.4 Hz), 6.85 (t, 2- CCHF$_2$, $^2J_{H-F}$=55.2 Hz), 4.03 (s, CH$_3$) ppm.

$^{19}$F NMR (376 MHz, CDCl$_3$; CFCl$_3$) δ=−113.99 (d, 2-CHF$_2$, $^2J_{F-H}$=55.3 Hz), −115.52 (d, 4-CHF$_2$, $^2J_{F-H}$=54.4 Hz) ppm.

$^{13}$C NMR (101 MHz, CDCl$_3$; Me$_4$Si) δ=159.77 (s, COCH$_3$), 149.93 (t, 2-C$_{arom}$, $^2J_{C-F}$=27.0 Hz), 143.966 (s, C8-C—N), 138.02 (t, 4-C$_{arom}$, $^2J_{C-F}$=22.0 Hz), 132.11 (s, 8-C$_{arom}$), 126.21 (s, C5-C—C4), 123.71 (s, 7-C$_{arom}$), 114.70 (tt, 3-C$_{arom}$, $^3J_{C-F}$=8.0, $^3J_{C-F}$=1.8 Hz), 114.51 (t, 2-CCHF$_2$, $^1J_{C-F}$=241.9 Hz), 113.57 (t, 4-CCHF$_2$, $^1J_{C-F}$=240.8 Hz), 101.35 (s, 5-C$_{arom}$), 55.79 (s, CH$_3$) ppm.

C$_{12}$H$_9$F$_4$NO (259): calcd (%) N, 5.40; C, 55.55; H, 3.47; found N, 5.43; C, 55.24; H, 3.30.

MP: 93.5-97.2° C.

EXAMPLE 44

4-(Difluoromethyl)-8-fluoro-2-(trifluoromethyl)quinoline (I-9)

1,1,2,2-Tetrafluoro-N,N-dimethylethan-1-amine (TFEDMA) was activated by adding boron trifluoride diethyl etherate (1.2 eq., 421 mg, 0.376 mL, 2.97 mmol) in a solution of TFEDMA (1.2 eq., 430 mg, 0.347 mL, 2.97 mmol) in dry acetonitrile (5 mL) and stirred for 15 min. Then a solution of 2-fluoro-N-(1,1,1-trifluoropropan-2-ylidene)aniline (II-5) (1 eq., 507 mg, 2.47 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-9) as a light brown solid in 70% yield (466 mg).

$^1$H NMR (400 MHz, CDCl$_3$; Me$_4$Si) δ=7.99 (s, 3-CH$_{arom}$), 7.94 (d, 5-CH$_{arom}$, $^3J_{H-H}$=8.6 Hz), 7.76 (td, 6-CH$_{arom}$, $^3J_{H-H}$=8.2, $^4J_{H-F}$=5.0 Hz), 7.63-7.55 (m, 7-CH$_{arom}$), 7.20 (t, 4-CCHF$_2$, $^2J_{H-F}$=54.1 Hz) ppm.

$^{19}$F NMR (376 MHz, CDCl$_3$; CFCl$_3$) δ=−67.64 (s, CF$_3$), −115.74 (d, 4-CHF$_2$, $^2J_{F-H}$=54.2 Hz), −119.97 (dd, F, $^3J_{F-H}$=10.5, $^4J_{F-H}$=5.4 Hz) ppm.

$^{13}$C NMR (101 MHz, CDCl$_3$; Me$_4$Si) δ=158.51 (d, 8-C$_{arom}$, $^1J_{C-F}$=261.9 Hz), 147.96 (qd, 2-C$_{arom}$, $^2J_{C-F}$=34.4

Hz, $^4J_{C-F}$=1.7 Hz), 140.33 (td, 4-C$_{arom}$, $^2J_{C-F}$=22.6, $^4J_{C-F}$=2.9 Hz), 138.40 (d, C8-C—N, $^2J_{C-F}$=12.2 Hz), 130.35 (d, 6-C$_{arom}$, $^3J_{C-F}$=8.1 Hz), 126.50 (s, C5-C—C4), 120.95 (q, 2-CCF$_3$, $^1J_{C-F}$=275.5 Hz), 119.25 (d, 5-C$_{arom}$, $^4J_{C-F}$=5.3 Hz), 115.90 (d, 7-C$_{arom}$, $^2J_{C-F}$=18.6 Hz), 115.20 (t, 3-C$_{arom}$, $^3J_{C-F}$=7.5 Hz), 112.48 (t, 4-CCHF$_2$, $^1J_{C-F}$=241.9 Hz) ppm.

C$_{11}$H$_5$F$_6$N (265): calcd (%) N, 5.28; C, 49.78; H, 1.88; found N, 5.44; C, 50.00; H, 1.95.

MP: 49.7-51.3° C.

EXAMPLE 45

2,4-Bis(difluoromethyl)-8-fluoroquinoline (I-10)

1,1,2,2-Tetrafluoro-N,N-dimethylethan-1-amine (TFEDMA) was activated by adding boron trifluoride diethyl etherate (1.2 eq., 457 mg, 0.408 mL, 3.22 mmol) in a solution of TFEDMA (1.2 eq., 467 mg, 0.377 mL, 3.22 mmol) in dry acetonitrile (5 mL) and stirred for 15 min. Then a solution of N-(1,1-difluoropropan-2-ylidene)-2-fluoroaniline (II-18) (1 eq., 502 mg, 2.68 mmol) in dry acetonitrile (5 mL) was slowly added to this mixture via syringe. After 15 min at room temperature, the mixture was heated at 50° C. for 19 h. Acetonitrile was removed under reduced pressure. The title compound (I-10) was isolated as yellow solid in mixture (3:1) with the 1,1,5,5-tetrafluoro-4-((2-fluorophenyl)amino)pent-3-en-2-one after purification using ethyl acetate in pentane (0-5%) in 39% yield (466 mg) (I-10).

$^1$H NMR (400 MHz, CDCl$_3$; Me$_4$Si) δ=8.00 (s, 3-CH$_{arom}$), 7.93 (d, 5-CH$_{arom}$, $^3J_{H-H}$=8.6 Hz), 7.73-7.68 (m, 6-CH$_{arom}$), 7.60-7.52 (m, 7-CH$_{arom}$), 7.17 (t, 4-CCHF$_2$, $^2J_{H-F}$=54.2 Hz), 6.86 (t, 2-CCHF$_2$, $^2J_{H-F}$=54.8 Hz) ppm.

HRMS (ESI positive) for C$_{11}$H$_7$F$_5$N [M+H]: calcd 248.0493; found 248.0499.

EXAMPLE 46

4-(Difluoromethyl)-7-fluoro-2-(trifluoromethyl)quinoline (I-11)

1,1,2,2-Tetrafluoro-N,N-dimethylethan-1-amine (TFEDMA) was activated by adding boron trifluoride diethyl etherate (1.2 eq., 422 mg, 0.378 mL, 2.98 mmol) in a solution of TFEDMA (1.2 eq., 432 mg, 0.349 mL, 2.98 mmol) in dry acetonitrile (5 mL) and stirred for 15 min. Then a solution of 3-fluoro-N-(1,1,1-trifluoropropan-2-ylidene)aniline (II-6) (1 eq., 509 mg, 2.48 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-11) as a yellow solid in 62% yield (405 mg).

$^1$H NMR (400 MHz, CDCl$_3$; Me$_4$Si) δ=8.19 (dd, 8-CH$_{arom}$, $^4J_{H-H}$=9.2, $^3J_{H-F}$=5.7 Hz), 7.93 (dd, 5-CH$_{arom}$, $^3J_{H-H}$=9.3, $^4J_{H-F}$=2.3 Hz), 7.88 (s, 3-CH$_{arom}$), 7.61-7.54 (m, 6-CH$_{arom}$), 7.17 (t, 4-CCHF$_2$, $^2J_{H-F}$=54.1 Hz) ppm.

$^{19}$F NMR (376 MHz, CDCl$_3$; CFCl$_3$) δ=−67.89 (s, CF$_3$), −105.57−−105.66 (m, F), −114.89 (d, 4-CHF$_2$, $^2J_{F-H}$=54.0 Hz) ppm.

$^{13}$C NMR (101 MHz, CDCl$_3$; Me$_4$Si) δ=163.84 (d, 7-C$_{arom}$, $^1J_{C-F}$=254.8 Hz), 149.36 (d, C8-C—N, $^3J_{C-F}$=13.1 Hz), 149.09 (q, 2-C$_{arom}$, $^2J_{C-F}$=35.6 Hz), 140.60 (td, 4-C$_{arom}$, $^2J_{C-F}$=22.5, $^5J_{C-F}$=1.4 Hz), 125.92 (d, 5-C$_{arom}$, $^3J_{C-F}$=9.8 Hz), 122.08 (s, C5-C—C4), 121.04 (q, 2-CCF$_3$, $^1J_{C-F}$=275.4 Hz), 120.77 (d, 6-C$_{arom}$, $^2J_{C-F}$=25.6 Hz), 114.89 (d, 8-C$_{arom}$, $^2J_{C-F}$=20.7 Hz), 113.92-113.16 (m, 3-C$_{arom}$), 112.81 (t, 4-CCHF$_2$, $^1J_{C-F}$=241.8 Hz) ppm.

C$_{11}$H$_5$F$_6$N (265): calcd (%) N, 5.28; C, 49.78; H, 1.88; found N, 5.36; C, 49.88; H 1.77.

MP: 61.6-62.8° C.

EXAMPLE 47

2,4-Bis(difluoromethyl)-7-fluoroquinoline (I-12)

1,1,2,2-Tetrafluoro-N,N-dimethylethan-1-amine (TFEDMA) was activated by adding boron trifluoride diethyl etherate (1.2 eq., 456 mg, 0.408 mL, 3.22 mmol) in a solution of TFEDMA (1.2 eq., 466 mg, 0.376 mL, 3.22 mmol) in dry acetonitrile (5 mL) and stirred for 15 min. Then a solution of N-(1,1-difluoropropan-2-ylidene)-3-fluoroaniline (II-19) (1 eq., 501 mg, 2.68 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-12) as a yellow solid in 70% yield (464 mg).

$^1$H NMR (400 MHz, CDCl$_3$; Me$_4$Si) δ=8.17 (dd, 8-CH$_{arom}$, $^4J_{H-H}$=9.3, $^3J_{H-F}$=5.7 Hz), 7.86 (s, 3-CH$_{arom}$), 7.84 (s, 5-CH$_{arom}$), 7.57-7.49 (m, 6-CH$_{arom}$), 7.14 (t, 4-CCHF$_2$, $^2J_{H-F}$=54.2 Hz), 6.78 (t, 2-CCHF$_2$, $^2J_{H-F}$=55.0 Hz) ppm.

$^{19}$F NMR (376 MHz, CDCl$_3$; CFCl$_3$) δ=−106.41−−106.96 (m, F), −114.43 (d, 2-CHF$_2$, $^2J_{F-H}$=54.2 Hz), −114.83 (d, 4-CHF$_2$, $^2J_{F-H}$=55.0 Hz) ppm.

$^{13}$C NMR (101 MHz, CDCl$_3$; Me$_4$Si) δ=163.60 (d, 7-C$_{arom}$, $^1J_{C-F}$=253.6 Hz), 153.93 (t, 2-C$_{arom}$, $^2J_{C-F}$=27.3 Hz), 149.21 (d, C8-C—N, $^3J_{C-F}$=12.7 Hz), 140.17 (td, 4-C$_{arom}$, $^2J_{C-F}$=22.4, $^5J_{C-F}$=1.1 Hz), 126.00 (d, 5-C$_{arom}$, $^3J_{C-F}$=9.8 Hz), 121.79 (d, C5-C—C4, $^4J_{C-F}$=1.0 Hz), 119.91 (d, 6-C$_{arom}$, $^2J_{C-F}$=25.39 Hz), 114.54 (d, 8-C$_{arom}$, $^2J_{C-F}$=20.56 Hz), 114.12 (t, 2-CCHF$_2$, $^1J_{C-F}$=242.9 Hz), 113.86 (m, 3-C$_{arom}$), 113.23 (t, 4-CCHF$_2$, $^1J_{C-F}$=241.5 Hz) ppm.

C$_{11}$H$_6$F$_5$N (247): calcd (%) N, 5.66; C, 53.41; H, 2.43; found N, 5.79; C, 53.54; H, 2.69.

MP: 73.2-74.6° C.

EXAMPLE 48

4-(Difluoromethyl)-6-fluoro-2-(trifluoromethyl)quinoline (I-13)

1,1,2,2-Tetrafluoro-N,N-dimethylethan-1-amine (TFEDMA) was activated by adding boron trifluoride diethyl etherate (1.2 eq., 419 mg, 0.374 mL, 2.96 mmol) in a solution of TFEDMA (1.2 eq., 428 mg, 0.346 mL, 2.96 mmol) in dry acetonitrile (5 mL) and stirred for 15 min. Then a solution of 4-fluoro-N-(1,1,1-trifluoropropan-2-ylidene)aniline (II-7) (1 eq., 505 mg, 2.46 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-13) as a yellow solid in 67% yield (434 mg).

$^1$H NMR (400 MHz, CDCl$_3$; Me$_4$Si) δ=8.32 (dd, 8-CH$_{arom}$, $^3J_{H-H}$=9.3, $^4J_{H-F}$=5.5 Hz), 7.93 (s, 3-CH$_{arom}$), 7.81-7.73 (m, 5-CH$_{arom}$), 7.67-7.66 (m, 7-CH$_{arom}$), 7.12 (t, 4-CCHF$_2$, $^2J_{H-F}$=54.1 Hz) ppm.

$^{19}$F NMR (376 MHz, CDCl$_3$; CFCl$_3$) δ=−67.69 (s, CF$_3$), −105.80 (td, F, $^3J_{F-H}$=8.6, $^4J_{F-H}$=5.7 Hz), −115.61 (d, 4-CHF$_2$, $^2J_{F-H}$=54.1 Hz) ppm.

$^{13}$C NMR (101 MHz, CDCl$_3$; Me$_4$Si) δ=162.40 (d, 6-C$_{arom}$, $^1J_{C-F}$=254.3 Hz), 147.31 (qd, 2-C$_{arom}$, $^2J_{C-F}$=35.7, $^6J_{C-F}$=3.2 Hz), 145.05 (s, C8-C—N), 139.92 (td, 4-C$_{arom}$, $^2J_{C-F}$=22.5, $^4J_{C-F}$=6.2 Hz), 133.96 (d, 8-C$_{arom}$, $^3J_{C-F}$=9.8 Hz), 126.06 (d, C5-C—C4, $^3J_{C-F}$=10.7 Hz), 122.01 (d, 7-C$_{arom}$, $^2J_{C-F}$=26.0 Hz), 121.24 (q, 2-CCF$_3$, $^1J_{C-F}$=275.1 Hz), 115.17-115.02 (m, 3-C$_{arom}$), 112.74 (t, 4-CCHF$_2$, $^1J_{C-F}$=237.4 Hz), 107.68 (d, 5-C$_{arom}$, $^2J_{C-F}$=24.1 Hz) ppm.

HRMS (ESI positive) for C$_{11}$H$_6$F$_6$N [M+H]: calcd 266.0399; found 266.0387.

MP: 68.2-69.8° C.

EXAMPLE 49

2,4-Bis(difluoromethyl)-6-fluoroquinoline (I-14)

1,1,2,2-Tetrafluoro-N,N-dimethylethan-1-amine (TFEDMA) was activated by adding boron trifluoride diethyl etherate (1.51 eq., 457 mg, 0.408 mL, 3.22 mmol) in a solution of TFEDMA (1.5 eq., 465 mg, 0.375 mL, 3.2 mmol) in dry acetonitrile (5 mL) and stirred for 15 min. Then a solution of N-(1,1-difluoropropan-2-ylidene)-4-fluoroaniline (II-20) (1 eq., 400 mg, 2.14 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-14) as a yellow solid in 39% yield (205 mg).

$^1$H NMR (400 MHz, CDCl$_3$; Me$_4$Si) δ=8.24 (dd, 8-CH$_{arom}$, $^3J_{H-H}$=9.3, $^4J_{H-H}$=5.5 Hz), 7.92 (s, 3-CH$_{arom}$), 7.80-7.74 (m, 5-CH$_{arom}$), 7.65-7.60 (m, 7-CH$_{arom}$), 7.09 (t, 4-CCHF$_2$, $^2J_{H-F}$=54.2 Hz), 6.79 (t, 2-CCHF$_2$, $^2J_{H-F}$=55.0 Hz) ppm.

$^{19}$F NMR (376 MHz, CDCl$_3$; CFCl$_3$) δ=−107.18--107.24 (m, F), −114.45 (d, 2-CHF$_2$, $^2J_{F-H}$=55.0 Hz), −115.17 (d, 4-CHF$_2$, $^2J_{F-H}$=54.2 Hz) ppm.

$^{13}$C NMR (101 MHz, CDCl$_3$; Me$_4$Si) δ=162.01 (d, 6-C$_{arom}$, $^1J_{C-F}$=252.9 Hz), 152.09 (td, 2-C$_{arom}$, $^2J_{C-F}$=27.3, $^6J_{C-F}$=3.1 Hz), 144.98 (s, C8-C—N), 139.56 (td, 4-C$_{arom}$, $^2J_{C-F}$=22.4, $^4J_{C-F}$=6.1 Hz), 133.46 (d, 8-C$_{arom}$, $^3J_{C-F}$=9.6 Hz), 125.76 (d, C5-C—C4, $^3J_{C-F}$=10.4 Hz), 121.43 (d, 7-C$_{arom}$, $^2J_{C-F}$=25.8 Hz), 115.28 (t, 3-C$_{arom}$, $^3J_{C-F}$=7.8 Hz), 114.21 (t, 2-CCHF$_2$, $^1J_{C-F}$=241.3 Hz), 110.78 (t, 4-CCHF$_2$, $^1J_{C-F}$=242.0 Hz), 107.84 (d, 5-C$_{arom}$, $^2J_{C-F}$=24.0 Hz) ppm.

C$_{11}$H$_6$F$_5$N (247): calcd (%) N, 5.66, C, 53.41, H, 2.43, found N, 5.67, C, 53.42, H, 2.57.

HRMS (ESI positive) for C$_{11}$H$_7$F$_5$N [M+H]: calcd 248.0493; found 248.0497.

MP: 68.7-71.2° C.

EXAMPLE 50

2,4-Bis(difluoromethyl)-8-(trifluoromethoxy)quinoline (I-15)

1,1,2,2-Tetrafluoro-N,N-dimethylethan-1-amine (TFEDMA) was activated by adding boron trifluoride diethyl etherate (1.44 eq., 414 mg, 0.37 mL, 2.92 mmol) in a solution of TFEDMA (1.44 eq., 421 mg, 0.34 mL, 2.91 mmol) in dry acetonitrile (5 mL) and stirred for 15 min. Then a solution of N-(1,1-difluoropropan-2-ylidene)-2-(trifluoromethoxy)aniline (II-21) (1 eq., 512 mg, 2.02 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-15) as a yellow solid in 39% yield (244 mg).

$^1$H NMR (400 MHz, CDCl$_3$; Me$_4$Si) δ=8.11 (dd, 7-CH$_{arom}$, $^3J_{H-H}$=8.1, $^4J_{H-H}$=1.4 Hz), 8.01 (s, 3-CH$_{arom}$), 7.76-7.75 (m, 5,6-CH$_{arom}$), 7.18 (t, 4-CCHF$_2$, $^2J_{H-F}$=54.1 Hz), 6.85 (t, 2-CCHF$_2$, $^2J_{H-F}$=54.8 Hz) ppm.

$^{19}$F NMR (376 MHz, CDCl$_3$; CFCl$_3$) δ=−57.55 (s, OCF$_3$), −114.12 (d, 2-CHF$_2$, $^2J_{F-H}$=54.9 Hz), −114.91 (d, 4-CHF$_2$, $^2J_{F-H}$=54.3 Hz) ppm.

$^{13}$C NMR (101 MHz, CDCl$_3$; Me$_4$Si) δ=153.55 (t, 2-C$_{arom}$, $^2J_{C-F}$=28.0 Hz), 146.06 (s, 8-C$_{arom}$), 141.11 (s, C8-C—N), 140.23 (t, 4-C$_{arom}$, $^2J_{C-F}$=22.5 Hz), 128.98 (s, 5-C$_{arom}$), 126.25 (s, C5-C—C4), 122.56 (s, 7-C$_{arom}$), 122.14 (s, 6-C$_{arom}$), 120.47 (q, OCF$_3$, $^1J_{C-F}$=259.6 Hz), 115.59 (t, 3-C$_{arom}$, $^3J_{C-F}$=7.9 Hz), 114.29 (t, 2-CCHF$_2$, $^1J_{C-F}$=242.4 Hz), 112.98 (t, 4-CCHF$_2$, $^1J_{C-F}$=241.7 Hz) ppm.

C$_{12}$H$_6$F$_7$NO (313): calcd (%) N, 4.47; C, 45.98; H, 1.92; found N, 4.57; C, 46.23; H, 1.98.

MP: 59.4-60° C.

EXAMPLE 51

4-(Difluoromethyl)-7-(trifluoromethoxy)-2-(trifluoromethyl)quinoline (I-16)

1,1,2,2-Tetrafluoro-N,N-dimethylethan-1-amine (TFEDMA) was activated by adding boron trifluoride diethyl etherate (1.2 eq., 314 mg, 0.28 mL, 2.21 mmol) in a solution of TFEDMA (1.2 eq., 321 mg, 0.259 mL, 2.21 mmol) in dry acetonitrile (5 mL) and stirred for 15 min. Then a solution of 3-(trifluoromethoxy)-N-(1,1,1-trifluoropropan-2-ylidene)aniline (II-9) (1 eq., 500 mg, 1.84 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-16) as a yellow solid in 36% yield (219 mg).

$^1$H NMR (400 MHz, CDCl$_3$; Me$_4$Si) δ=8.24 (d, 5-CH$_{arom}$, $^3J_{H-H}$=9.3 Hz), 8.16 (s, 8-CH$_{arom}$), 7.94 (s, 3-CH$_{arom}$), 7.65 (dd, 6-CH$_{arom}$, $^3J_{H-H}$=9.3, $^4J_{H-H}$=2.4 Hz), 7.18 (t, 4-CCHF$_2$, $^2J_{H-F}$=54.1 Hz) ppm.

$^{19}$F NMR (376 MHz, CDCl$_3$; CFCl$_3$) δ=−57.88 (s, OCF$_3$), −67.89 (s, CF$_3$), −114.87 (d, 4-CHF$_2$, $^2J_{F-H}$=54.1 Hz) ppm.

$^{13}$C NMR (101 MHz, CDCl$_3$; Me$_4$Si) δ=151 (s, 7-C$_{arom}$), 149.37 (q, 2-C$_{arom}$, $^2J_{C-F}$=35.8 Hz), 148.63 (s, C8-C—N), 140.65 (t, 4-C$_{arom}$, $^2J_{C-F}$=22.6 Hz), 125.80 (s, 5-C$_{arom}$), 123.99 (s, 6-C$_{arom}$), 123.23-123.19 (m, C5-C—C4), 121.07 (q, 2-CCF$_3$, $^1J_{C-F}$=276.7 Hz), 120.55 (q, OCF$_3$, $^1J_{C-F}$=260.0 Hz), 120.25 (s, 8-C$_{arom}$), 114.60 (td, 3-C$_{arom}$, $^3J_{C-F}$=8.0, $^3J_{C-F}$=2.0 Hz), 112.72 (t, 4-CCHF$_2$, $^1J_{C-F}$=242.0 Hz) ppm.

C$_{12}$H$_5$F$_8$NO (331): calcd (%) N, 4.23; C, 43.48; H, 1.51; found N, 4.28; C, 43.94; H, 1.35.

MP: 36.3-37.8° C.

EXAMPLE 52

2,4-Bis(difluoromethyl)-7-(trifluoromethoxy)quinoline (I-17)

1,1,2,2-Tetrafluoro-N,N-dimethylethan-1-amine (TFEDMA) was activated by adding boron trifluoride diethyl etherate (1.2 eq., 337 mg, 0.301 mL, 2.38 mmol) in a solution of TFEDMA (1.2 eq., 344 mg, 0.278 mL, 2.38 mmol) in dry acetonitrile (5 mL) and stirred for 15 min.

Then a solution of N-(1,1-difluoropropan-2-ylidene)-3-(trifluoromethoxy)aniline (II-22) (1 eq., 501 mg, 1.98 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-17) as a light brown liquid in 71% yield (440 mg).

$^1$H NMR (400 MHz, CDCl$_3$; Me$_4$Si) δ=8.08 (d, 5-CH$_{arom}$, $^3$J$_{H-H}$=9.2 Hz), 7.93 (s, 8-CH$_{arom}$), 7.79 (s, 3-CH$_{arom}$), 7.46 (d, 6-CH$_{arom}$, $^3$J$_{H-H}$=9.2 Hz), 7.03 (t, 4-CCHF$_2$, $^2$J$_{H-F}$=54.2 Hz), 6.69 (t, 2-CCHF$_2$, $^2$J$_{H-F}$=55.0 Hz) ppm.

$^{19}$F NMR (376 MHz, CDCl$_3$; CFCl$_3$) δ=−58.14 (s, OCF$_3$), −114.72 (d, 2-CHF$_2$, $^2$J$_{F-H}$=54.1 Hz), −115.17 (d, 4-CHF$_2$, $^2$J$_{F-H}$=54.9 Hz) ppm.

$^{13}$C NMR (101 MHz, CDCl$_3$; Me$_4$Si) δ=154.12 (t, 2-C$_{arom}$, $^2$J$_{C-F}$=27.3 Hz), 150.58 (s, 7-C$_{arom}$), 148.46 (s, C8-C—N), 140.14 (t, 4-C$_{arom}$, $^2$J$_{C-F}$=22.5 Hz), 125.76 (s, 5-C$_{arom}$), 123.13 (s, 6-C$_{arom}$), 122.95 (s, C5-C—C4), 120.58 (q, OCF$_3$, $^1$J$_{C-F}$=259.4 Hz), 120.02 (s, 8-C$_{arom}$), 114.72 (tt, 3-C$_{arom}$, $^3$J$_{C-F}$=8, $^3$J$_{C-F}$=1.8 Hz), 114.04 (t, 2-CCHF$_2$, $^1$J$_{C-F}$=242.4 Hz), 113.12 (t, 4-CCHF$_2$, $^1$J$_{C-F}$=241.4 Hz) ppm.

C$_{12}$H$_6$F$_7$NO (313): calcd (%) N, 4.47; C, 45.98; H, 1.92; found N, 4.49; C, 46.13; H 2.15.

EXAMPLE 53

4-(Difluoromethyl)-6-(trifluoromethoxy)-2-(trifluoromethyl)quinoline (I-18)

1,1,2,2-Tetrafluoro-N,N-dimethylethan-1-amine (TFEDMA) was activated by adding boron trifluoride diethyl etherate (1.2 eq., 315 mg, 0.282 mL, 2.22 mmol) in a solution of TFEDMA (1.2 eq., 344 mg, 0.278 mL, 2.38 mmol) in dry acetonitrile (5 mL) and stirred for 15 min. Then a solution of 4-(trifluoromethoxy)-N-(1,1,1-trifluoropropan-2-ylidene)aniline (II-10) (1 eq., 584 mg, 1.85 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-18) as a yellow solid in 49% yield (300.3 mg).

$^1$H NMR (400 MHz, CDCl$_3$; Me$_4$Si) δ=8.39 (d, 8-CH$_{arom}$, $^3$J$_{H-H}$=9.3 Hz), 7.97 (s, 3,5-CH$_{arom}$), 7.77 (dd, 7-CH$_{arom}$, $^3$J$_{H-H}$=9.3, $^4$J$_{H-H}$=1.9 Hz), 7.15 (t, 4-CCHF$_2$, $^2$J$_{H-F}$=54.0 Hz) ppm.

$^{19}$F NMR (376 MHz, CDCl$_3$; CFCl$_3$) δ=−57.72 (s, OCF$_3$), −67.79 (s, CF$_3$), −115.31 (d, 4-CHF$_2$, $^2$J$_{F-H}$=53.9 Hz) ppm.

$^{13}$C NMR (101 MHz, CDCl$_3$; Me$_4$Si) δ=149.50 (s, 6-C$_{arom}$), 148.41 (q, 2-C$_{arom}$, $^2$J$_{C-F}$=35.9 Hz), 146.02 (s, C8-C—N), 140.46 (t, 4-C$_{arom}$, $^2$J$_{C-F}$=22.6 Hz), 133.66 (s, 8-C$_{arom}$), 125.52 (s, C5-C—C4), 125.35 (s, 7-C$_{arom}$), 121.12 (q, 2-CCF$_3$, $^1$J$_{C-F}$=276.4 Hz), 120.74 (q, OCF$_3$, $^1$J$_{C-F}$=260.6 Hz), 115.36 (td, 3-C$_{arom}$, $^3$J$_{C-F}$=8.0, $^3$J$_{C-F}$=2.1 Hz), 113.97 (s, 5-C$_{arom}$), 112.67 (t, 4-CCHF$_2$, $^1$J$_{C-F}$=242.0 Hz) ppm.

C$_{12}$H$_5$F$_8$NO (331): calcd (%) N, 4.23; C, 43.48; H, 1.51; found N, 4.20; C, 43.77; H, 1.83.

MP: 42.2-43.8° C.

EXAMPLE 54

2,4-Bis(difluoromethyl)-6-(trifluoromethoxy)quinoline (I-19)

1,1,2,2-Tetrafluoro-N,N-dimethylethan-1-amine (TFEDMA) was activated by adding boron trifluoride diethyl etherate (1.51 eq., 422 mg, 0.378 mL, 2.98 mmol) in a solution of TFEDMA (1.5 eq., 429 mg, 0.347 mL, 2.96 mmol) in dry acetonitrile (5 mL) and stirred for 15 min. Then a solution of N-(1,1-difluoropropan-2-ylidene)-4-(trifluoromethoxy)aniline (II-23) (1 eq., 500 mg, 1.98 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-19) as a yellow solid in 58% yield (361 mg).

$^1$H NMR (400 MHz, CDCl$_3$; Me$_4$Si) δ=8.30 (d, 8-CH$_{arom}$, $^3$J$_{H-H}$=9.3 Hz), 7.96-7.95 (m, 3,5-CH$_{arom}$), 7.73 (dd, 7-CH$_{arom}$, $^3$J$_{H-H}$=9.3, $^4$J$_{H-H}$=1.8 Hz), 7.13 (t, 4-CCHF$_2$, $^2$J$_{H-F}$=56.0 Hz), 6.80 (t, 2-CCHF$_2$, $^2$J$_{H-F}$=55.0 Hz) ppm.

$^{19}$F NMR (376 MHz, CDCl$_3$; CFCl$_3$) δ=−57.71 (s, OCF$_3$), −114.67 (d, 2-CHF$_2$, $^2$J$_{F-H}$=55.0 Hz), −114.88 (d, 4-CHF$_2$, $^2$J$_{F-H}$=54.1 Hz) ppm.

$^{13}$C NMR (101 MHz, CDCl$_3$; Me$_4$Si) δ=153.23 (t, 2-C$_{arom}$, $^2$J$_{C-F}$=27.5 Hz), 148.97 (s, 6-C$_{arom}$), 146.01 (s, C8-C—N), 140.06 (t, 4-C$_{arom}$, $^2$J$_{C-F}$=22.5 Hz), 133.17 (s, 8-C$_{arom}$), 125.23 (s, C5-C—C4), 124.89 (s, 7-C$_{arom}$), 120.59 (q, OCF$_3$, $^1$J$_{C-F}$=259.2 Hz), 115.64-115.49 (m, 3-C$_{arom}$), 114.32 (s, 5-C$_{arom}$), 114.08 (t, 2-CCHF$_2$, $^1$J$_{C-F}$=241.6 Hz), 113.09 (t, 4-CCHF$_2$, $^1$J$_{C-F}$=240.0 Hz) ppm.

C$_{12}$H$_6$F$_7$NO (313): calcd (%) N, 4.47; C, 45.98; H, 1.92; found N, 4.49; C, 46.35; H, 2.07.

MP: 47.5-48.2° C.

EXAMPLE 55

2,4-Bis(difluoromethyl)-N,N-dimethylquinolin-7-amine (I-20)

1,1,2,2-Tetrafluoro-N,N-dimethylethan-1-amine (TFEDMA) was activated by adding boron trifluoride diethyl etherate (1.2 eq., 401 mg, 0.358 mL, 2.83 mmol) in a solution of TFEDMA (1.2 eq., 410 mg, 0.331 mL, 2.83 mmol) in dry acetonitrile (5 mL) and stirred for 15 min. Then a solution of 3-N-(1,1-difluoropropan-2-ylidene)-1-N,N-dimethylbenzene-1,3-diamine (II-24) (1 eq., 500 mg, 2.36 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-20) as a brown solid in 15% yield (98.2 mg).

$^1$H NMR (400 MHz, CDCl$_3$; Me$_4$Si) δ=7.94 (d, 5-CH$_{arom}$, $^3$J$_{H-H}$=9.4 Hz), 7.55 (s, 8-CH$_{arom}$), 7.29 (dd, 6-CH$_{arom}$, $^3$J$_{H-H}$=9.4, $^4$J$_{H-H}$=2.7 Hz), 7.21 (d, 3-CH$_{arom}$, J=2.7 Hz), 7.08 (t, 4-CCHF$_2$, $^2$J$_{H-F}$=54.6 Hz), 6.72 (t, 2-CCHF$_2$, $^2$J$_{H-F}$=55.4 Hz), 3.13 (s, N—(CH$_3$)$_2$) ppm.

$^{19}$F NMR (376 MHz, CDCl$_3$; CFCl$_3$) δ=−114.59 (d, 2-CHF$_2$, $^2$J$_{F-H}$=54.6 Hz), −114.89 (d, 4-CHF$_2$, $^2$J$_{F-H}$=.4 Hz) ppm.

$^{13}$C NMR (101 MHz, CDCl$_3$; Me$_4$Si) δ=152.95 (t, 2-C$_{arom}$, $^b$ $^2$J$_{C-F}$=26.5 Hz), 151.69 (s, 7-C$_{arom}$), 150.03 (s, C8-C—N), 139.30 (t, 4-C$_{arom}$, $^2$J$_{C-F}$=23.9 Hz), 124.08 (s, 5-C$_{arom}$), 118.49 (s, 8-C$_{arom}$), 116.98 (s, C5-C—C4), 114.56 (t, 2-CCHF$_2$, $^1$J$_{C-F}$=264.0 Hz), 113.54 (t, 4-CCHF$_2$, $^1$J$_{C-F}$=240.8 Hz), 109.73 (tt, 3-C$_{arom}$, $^3$ J$_{C-F}$=8.0, $^3$J$_{C-F}$=2.2 Hz), 107.26 (s, 6-C$_{arom}$), 40.38 (s, N—(CH$_3$)$_2$) ppm.

C$_{13}$H$_{12}$F$_4$N$_2$ (272): calcd (%) N, 10.20; C, 57.30; H, 4.41; found N, 10.06; C, 57.26; H, 4.41.

MP: 83.7-84.7° C.

EXAMPLE 56

4-(Difluoromethyl)-N,N-dimethyl-2-(trifluoromethyl)quinolin-6-amine (I-21)

1,1,2,2-Tetrafluoro-N,N-dimethylethan-1-amine (TFEDMA) was activated was activated by adding boron trifluoride diethyl etherate (1.2 eq., 369 mg, 0.33 mL, 2.61 mmol) in a solution of TFEDMA (1.2 eq., 378 mg, 0.305 mL, 2.61 mmol) in dry acetonitrile (5 mL) and stirred for 15 min. Then a solution of 1-N,N-dimethyl-4-N-(1,1,1-trifluoropropan-2-ylidene)benzene-1,4-diamine (II-11) (1 eq., 500 mg, 2.17 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-21) as a yellow solid in 37% yield (235 mg).

$^1$H NMR (400 MHz, CDCl$_3$; Me$_4$Si) δ=8.07 (d, 8-CH$_{arom}$, $^3J_{H-H}$=9.5 Hz), 7.75 (s, 3-CH$_{arom}$), 7.43 (dd, 7-CH$_{arom}$, $^3J_{H-H}$=9.5, $^4J_{H-H}$=2.8 Hz), 7.07 (t, 4-CCHF$_2$, $^2J_{H-F}$=54.5 Hz), 6.84 (s, 5-CH$_{arom}$), 3.14 (s, N—(CH$_3$)$_2$) ppm.

$^{19}$F NMR (376 MHz, CDCl$_3$; CFCl$_3$) δ=−66.90 (s, CF$_3$), −117.13 (d, 4-CHF$_2$, $^2J_{F-H}$=54.7 Hz) ppm.

$^{13}$C NMR (101 MHz, CDCl$_3$; Me$_4$Si) δ=150.28 (s, 6-C$_{arom}$), 143.01-141.69 (m, 2-C$_{arom}$+C8-C—N), 136.12 (t, 4-C$_{arom}$, $^2J_{C-F}$=21.6 Hz), 131.80 (s, 8-C$_{arom}$), 127.25 (t, C5-C—C4, $^3J_{C-F}$=2.5 Hz), 121.98 (q, 2-CCF$_3$, $^1J_{C-F}$=274.0 Hz), 120.46 (s, 7-C$_{arom}$), 114.48 (td, 3-C$_{arom}$, $^3J_{C-F}$=8.2, $^3J_{C-F}$=2.3 Hz), 113.29 (t, 4-CCHF$_2$, $^1J_{C-F}$=240.4 Hz), 98.92 (s, 5-C$_{arom}$), 40.46 (s, N—(CH$_3$)$_2$) ppm.

C$_{13}$H$_{11}$F$_5$N$_2$ (290): calcd (%) N, 9.65; C, 53.75; H, 3.79; found N, 9.42; C, 53.55; H, 3.81.

MP: 107.5-108.4° C.

EXAMPLE 57

2,4-Bis(difluoromethyl)-N,N-dimethylquinolin-6-amine (I-22)

1,1,2,2-Tetrafluoro-N,N-dimethylethan-1-amine (TFEDMA) was activated by adding boron trifluoride diethyl etherate (1.2 eq., 401 mg, 0.358 mL, 2.83 mmol) in a solution of TFEDMA (1.2 eq., 410 mg, 0.331 mL, 2.83 mmol) in dry acetonitrile (5 mL) and stirred for 15 min. Then a solution of 4-N-(1,1-difluoropropan-2-ylidene)-1-N,N-dimethylbenzene-1,4-diamine (II-25) (1 eq., 500 mg, 2.36 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-22) as an orange solid in 14% yield (91.9 mg).

$^1$H NMR (400 MHz, CDCl$_3$; Me$_4$Si) δ=8.01 (d, 8-CH$_{arom}$, $^3J_{H-H}$=9.4 Hz), 7.76 (s, 3-CH$_{arom}$), 7.42 (dd, 7-CH$_{arom}$, $^3J_{H-H}$=9.5, $^4J_{H-H}$=2.7 Hz), 7.07 (t, 4-CCHF$_2$, $^2J_{H-F}$=54.6 Hz), 6.90 (s, 5-CH$_{arom}$), 6.75 (t, 2-CCHF$_2$, $^2J_{H-F}$=55.5 Hz), 3.14 (s, N—(CH$_3$)$_2$) ppm.

$^{19}$F NMR (376 MHz, CDCl$_3$; CFCl$_3$) δ=−113.38 (d, 2-CHF$_2$, $^2J_{F-H}$=55.5 Hz), −116.67 (d, 4-CHF$_2$, $^2J_{F-H}$=54.6 Hz) ppm.

$^{13}$C NMR (101 MHz, CDCl$_3$; Me$_4$Si) δ=149.96 (s, 6-C$_{arom}$), 147.42 (t, 2-C$_{arom}$, $^2J_{C-F}$=26.8 Hz), 141.73 (s, C8-C—N), 136.29 (t, 4-C$_{arom}$, $^2J_{C-F}$=21.5 Hz), 131.36 (s, 8-C$_{arom}$), 126.89 (s, C5-C—C4), 120.03 (s, 7-C$_{arom}$), 114.90 (t, 2-CCHF$_2$, $^1J_{C-F}$=239.9 Hz), 114.64 (t, 3-C$_{arom}$, $^3J_{C-F}$=8.1 Hz), 113.69 (t, 4-CCHF$_2$, $^1J_{C-F}$=241.4 Hz), 99.55 (s, 5-C$_{arom}$), 40.53 (s, N—(CH$_3$)$_2$) ppm.

C$_{13}$H$_{12}$F$_4$N$_2$ (272): calcd (%) N, 10.20; C, 57.30; H, 4.41; found N, 10.09; C, 56.86; H, 4.40.

MP: 115.6-116.9° C.

EXAMPLE 58

4-(Difluoromethyl)-7-fluoro-8-methyl-2-(trifluoromethyl)quinoline (I-23)

1,1,2,2-Tetrafluoro-N,N-dimethylethan-1-amine (TFEDMA) was activated by adding boron trifluoride diethyl etherate (1.2 eq., 0.781 g, 0.698 mL, 5.5 mmol) in a solution of TFEDMA (1.2 eq., 0.799 g, 0.644 mL, 5.5 mmol) in dry acetonitrile (5 mL) and stirred for 15 min. Then a solution of 3-fluoro-2-methyl-N-(1,1,1-trifluoropropan-2-ylidene)aniline (II-12) (1 eq., 1.76 g, 4.59 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-23) as a yellow solid in 38% yield (488.4 mg).

$^1$H NMR (400 MHz, CDCl$_3$; Me$_4$Si) δ=7.99 (dd, 5-CH$_{arom}$, $^3J_{H-H}$=9.0, $^4J_{H-F}$=5.9 Hz), 7.88 (s, 3-CH$_{arom}$), 7.54 (t, 6-CH$_{arom}$, $^3J_{H-H}$=9.0 Hz), 7.17 (t, 4-CCHF$_2$, $^2J_{H-F}$=54.2 Hz), 2.75 (d, CH$_3$, $^4J_{H-F}$=2.6 Hz) ppm.

$^{19}$F NMR (376 MHz, CDCl$_3$; CFCl$_3$) δ=−67.78 (s, CF$_3$), −108.31−−108.46 (m, F), −114.94 (d, 4-CHF$_2$, $^2J_{F-H}$=54.2 Hz) ppm.

$^{13}$C NMR (101 MHz, CDCl$_3$; Me$_4$Si) δ=161.60 (d, 7-C$_{arom}$, $^1J_{C-F}$=250.2 Hz), 148.47-147.14 (m, 2-C$_{arom}$+C8-C—N), 140.54 (td, 4-C$_{arom}$, $^2J_{C-F}$=22.3, $^5J_{C-F}$=1.8 Hz), 123.79 (d, 8-C$_{arom}$, $^2J_{C-F}$=16.2 Hz), 122.26 (d, C5-C—C4+5-C$_{arom}$, $^3J_{C-F}$=10.3 Hz), 121.32 (q, 2-CCF$_3$, $^1J_{C-F}$=275.3 Hz), 120.25 (d, 6-C$_{arom}$, $^2J_{C-F}$=27.2 Hz), 113.49-112.94 (m, 3-C$_{arom}$), 112.84 (t, 4-CCHF$_2$, $^1J_{C-F}$=241.6 Hz), 9.38 (d, CH$_3$, $^3J_{C-F}$=3.7 Hz) ppm.

HRMS (ESI positive) for C$_{12}$H$_8$F$_6$N [M+H]: calcd 280.0555; found 280.0570.

MP: 78.7-79.4° C.

EXAMPLE 59

2,4-Bis(difluoromethyl)-7-fluoro-8-methylquinoline (I-24)

1,1,2,2-Tetrafluoro-N,N-dimethylethan-1-amine (TFEDMA) was activated by adding boron trifluoride diethyl etherate (1.2 eq., 0.847 g, 0.756 mL, 5.96 mmol) in a solution of TFEDMA (1.2 eq., 0.865 g, 0.698 mL, 5.96 mmol) in dry acetonitrile (5 mL) and stirred for 15 min. Then a solution of N-(1,1-difluoropropan-2-ylidene)-3-fluoro-2-methylaniline (II-26) (1 eq., 1 g, 4.97 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-24) as a yellow solid in 76% yield (990 mg).

$^1$H NMR (400 MHz, CDCl$_3$; Me$_4$Si) δ=7.96 (dd, 5-CH$_{arom}$, $^3J_{H-H}$=9.0, $^4J_{H-F}$=5.9 Hz), 7.86 (s, 3-CH$_{arom}$), 7.47 (t, 6-CH$_{arom}$, $^3J_{H-H}$=9.0 Hz), 7.13 (t, 4-CCHF$_2$, $^2J_{H-F}$=54.3 Hz), 6.81 (t, 2-CCHF$_2$, $^2J_{H-F}$=55.1 Hz), 2.71 (d, CH$_3$, $^4J_{H-F}$=2.5 Hz) ppm.

¹⁹F NMR (376 MHz, CDCl₃; CFCl₃) δ=−109.41 (ddd, F, $^3J_{H-F}$=8.4, $^4J_{H-F}$=5.6, $^4J_{CH3-F}$=2.7 Hz), −114.20 (d, 2-CHF₂, $^2J_{H-F}$=55.1 Hz), −114.56 (d, 4-CHF₂, $^2J_{H-F}$=54.3 Hz) ppm.

¹³C NMR (101 MHz, CDCl₃; Me₄Si) δ=161.37 (d, 7-C$_{arom}$, $^1J_{C-F}$=249.1 Hz), 152.53 (t, 2-C$_{arom}$, $^2J_{C-F}$=27.5 Hz), 148.08 (d, C8-C—N, $^3J_{C-F}$=10.1 Hz), 140.19 (t, 4-C$_{arom}$, $^2J_{C-F}$=21.5 Hz), 123.23 (d, 8-C$_{arom}$, $^2J_{C-F}$=16.1 Hz), 122.36 (d, 5-C$_{arom}$, $^3J_{C-F}$=10.2 Hz), 121.85 (s, C5-C—C4), 119.38 (d, 6-C$_{arom}$, $^2J_{C-F}$=27.0 Hz), 114.58 (t, 2-CCHF₂, $^1J_{C-F}$=241.2 Hz), 113.12 (t, 4-CCHF₂, $^1J_{C-F}$=242.4 Hz), 113.12 (s, 3-C$_{arom}$), 9.34 (d, CH₃, $^4J_{H-F}$=3.8 Hz) ppm.

C₁₂H₈F₅N (261): calcd (%) N, 5.36; C, 55.13; H, 3.06; found N, 5.26; C, 55.13; H, 3.22.

MP: 87.7-89° C.

EXAMPLE 60

7-Chloro-4-(difluoromethyl)-8-methyl-2-(trifluoromethyl)quinoline (I-25)

1,1,2,2-Tetrafluoro-N,N-dimethylethan-1-amine (TFEDMA) was activated by adding boron trifluoride diethyl etherate (1.2 eq., 0.726 g, 0.648 mL, 5.12 mmol) in a solution of TFEDMA (1.2 eq., 0.742 g, 0.599 mL, 5.12 mmol) in dry acetonitrile (5 mL) and stirred for 15 min. Then a solution of 3-chloro-2-methyl-N-(1,1,1-trifluoropropan-2-ylidene)aniline (II-13) (1 eq., 2.01 g, 4.26 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-25) as a beige amorphous solid in 38% yield (485 mg).

¹H NMR (400 MHz, CDCl₃; Me₄Si) δ=7.93-7.91 (m, 5-CH$_{arom}$+3-CH$_{arom}$), 7.74 (d, 6-CH$_{arom}$, $^3J_{H-H}$=9.1 Hz), 7.17 (t, 4-CCHF₂, $^2J_{H-F}$=54.2 Hz), 2.93 (s, CH₃) ppm.

¹⁹F NMR (376 MHz, CDCl₃; CFCl₃) δ=−67.78 (s, CF₃), −115.12 (d, 4-CHF₂, $^2J_{F-H}$=54.1 Hz) ppm.

¹³C NMR (101 MHz, CDCl₃; Me₄Si) δ=147.53 (q, 2-C$_{arom}$, $^2J_{C-F}$=35.8 Hz), 147.44 (s, C8-C—N), 140.63 (t, 4-C$_{arom}$, $^2J_{C-F}$=22.3 Hz), 137.44 (s, 7-C$_{arom}$), 137.10 (s, 8-C$_{arom}$), 131.35 (s, 6-C$_{arom}$), 121.50 (s, 5C$_{arom}$), 121.27 (q, 2-CCF₃, $^1J_{C-F}$=275.3 Hz), 119.32 (s, C5-C—C4), 113.93-113.73 (m, 3-C$_{arom}$), 112.70 (t, 4-CCHF₂, $^1J_{C-F}$=241.7 Hz), 14.91 (s, CH₃) ppm.

C₁₂H₇F₅NCl (295): calcd (%) N, 4.73; C, 48.70; H, 2.36; found N, 4.62; C, 48.82; H, 2.55.

EXAMPLE 61

7-Chloro-2,4-bis(difluoromethyl)-8-methylquinoline (I-26)

1,1,2,2-Tetrafluoro-N,N-dimethylethan-1-amine (TFEDMA) was activated by adding boron trifluoride diethyl etherate (1.2 eq., 0.804 g, 0.717 mL, 5.66 mmol) in a solution of TFEDMA (1.2 eq., 0.821 g, 0.662 mL, 5.66 mmol) in dry acetonitrile (5 mL) and stirred for 15 min. Then a solution of 3-chloro-N-(1,1-difluoropropan-2-ylidene)-2-methylaniline (II-27) (1 eq., 1.03 g, 4.72 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-26) as a colourless solid in 75% yield (977 mg).

¹H NMR (400 MHz, CDCl₃; Me₄Si) δ=7.89-7.88 (m, 5-CH$_{arom}$+3-CH$_{arom}$), 7.67 (d, 6-CH$_{arom}$, $^3J_{H-H}$=9.1 Hz), 7.13 (t, 4-CCHF₂, $^2J_{H-F}$=54.3 Hz), 6.80 (t, 2-CCHF₂, $^2J_{H-F}$=55.1 Hz), 2.88 (s, CH₃) ppm.

¹⁹F NMR (376 MHz, CDCl₃; CFCl₃) δ=−114.17 (d, 2-CHF₂, $^2J_{F-H}$=55.1 Hz), −114.75 (d, 4-CHF₂, $^2J_{F-H}$=54.3 Hz) ppm.

¹³C NMR (101 MHz, CDCl₃; Me₄Si) δ=152.34 (t, 2-C$_{arom}$, $^2J_{C-F}$=27.6 Hz), 147.27 (s, C8-C—N), 140.27 (t, 4-C$_{arom}$, $^2J_{C-F}$=22.2 Hz), 136.83 (s, 7-C$_{arom}$), 136.57 (s, 8-C$_{arom}$), 130.56 (s, 6-C$_{arom}$), 123.48 (s, C5-C—C4), 121.65 (s, 5-C$_{arom}$), 114.52 (t, 2-CCHF₂, $^1J_{C-F}$=241.3 Hz), 113.97 (t, 3-C$_{arom}$, $^3J_{C-F}$=7.9 Hz), 113.08 (t, 4-CCHF₂, $^1J_{C-F}$=242.4 Hz), 14.84 (s, CH₃) ppm.

C₁₂H₈F₄NCl (277): calcd (%) N, 5.04; C, 51.86; H, 2.88; found N, 4.92; C, 52.02; H, 3.03.

MP: 58.9-59.5° C.

EXAMPLE 62

7-Chloro-2,4-bis(difluoromethyl)quinoline (I-27)

1,1,2,2-Tetrafluoro-N,N-dimethylethan-1-amine (TFEDMA) was activated by adding boron trifluoride diethyl etherate (1.2 eq., 4.18 g, 3.73 mL, 29.5 mmol) in a solution of TFEDMA (1.2 eq., 4.28 g, 3.45 mL, 29.5 mmol) in dry acetonitrile (5 mL) and stirred for 15 min. Then a solution of 3-chloro-N-(1,1-difluoropropan-2-ylidene)aniline (II-29) (1 eq., 5 g, 24.6 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-27) as a colourless solid in 45% yield (2.93 g).

¹H NMR (400 MHz, CDCl₃; Me₄Si) δ=8.20 (d, 8-CH$_{arom}$, $^4J_{H-H}$=2.1 Hz), 8.07 (d, 5-CH$_{arom}$, $^3J_{H-H}$=9.0 Hz), 7.88 (s, 3-CH$_{arom}$), 7.67 (dd, 6-CH$_{arom}$, $^3J_{H-H}$=9.0, $^4J_{H-H}$=2.1 Hz), 7.12 (t, 4-CCHF₂, $^2J_{H-F}$=54.2 Hz), 6.77 (t, 2-CCHF₂, $^2J_{H-F}$=55.0 Hz) ppm.

¹⁹F NMR (376 MHz, CDCl₃; CFCl₃) δ=−114.58--114.87 (m, 2-CHF₂+4-CHF₂) ppm.

¹³C NMR (101 MHz, CDCl₃; Me₄Si) δ=153.83 (t, 2-C$_{arom}$, $^2J_{C-F}$=27.3 Hz), 148.27 (s, C8-C—N), 140.12 (t, 4-C$_{arom}$, $^2J_{C-F}$=22.4 Hz), 137.12 (s, 7-C$_{arom}$), 130.33 (s, 6-C$_{arom}$), 129.71 (s, 8-C$_{arom}$), 124.95 (s, 5-C$_{arom}$), 123.13 (s, C5-C—C4), 114.58 (tt, 3-C$_{arom}$, $^3J_{C-F}$=8, $^3J_{C-F}$=1.8 Hz), 114.09 (t, 2-CCHF₂, $^1J_{C-F}$=242.9 Hz), 113.08 (t, 4-CCHF₂, $^1J_{C-F}$=241.5 Hz) ppm.

C₁₁H₆F₄NCl (263): calcd (%) N, 5.31; C, 50.12; H, 2.29; found N, 5.23; C, 50.00; H, 2.29.

MP: 90.2-91° C.

EXAMPLE 63

2,4-Bis(difluoromethyl)-7-(trifluoromethyl)quinoline (I-28)

1,1,2,2-Tetrafluoro-N,N-dimethylethan-1-amine (TFEDMA) was activated by adding boron trifluoride diethyl etherate (1.2 eq., 0.679 g, 0.606 mL, 4.79 mmol) in a solution of TFEDMA (1.2 eq., 0.694 g, 0.56 mL, 4.79 mmol) in dry acetonitrile (5 mL) and stirred for 15 min. Then a solution of N-(1,1-difluoropropan-2-ylidene)-3-(trifluoromethyl)aniline (II-30) (1 eq., 0.946 g, 3.99 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-28) as a colourless solid in 28% yield (328.5 mg).

$^1$H NMR (400 MHz, CDCl$_3$; Me$_4$Si) δ=8.56 (s, 8-CH$_{arom}$), 8.31 (d, 5-CH$_{arom}$, $^3J_{H-H}$=8.9 Hz), 8.02 (s, 3-CH$_{arom}$), 7.93 (d, 6-CH$_{arom}$, $^3J_{H-H}$=8.7 Hz), 7.19 (t, 4-CCHF$_2$, $^2J_{H-F}$=54.1 Hz), 6.82 (t, 2-CCHF$_2$, $^2J_{H-F}$=54.9 Hz) ppm.

$^{19}$F NMR (376 MHz, CDCl$_3$; CFCl$_3$) δ=−63.10 (s, CF$_3$), −114.71 (d, 2-CHF$_2$, $^2J_{F-H}$=56.4 Hz), −114.81 (d, 4-CHF$_2$, $^2J_{F-H}$=54.8 Hz) ppm.

$^{13}$C NMR (101 MHz, CDCl$_3$; Me$_4$Si) δ=154.19 (t, 2-C$_{arom}$, $^2J_{C-F}$=27.5 Hz), 146.86 (s, C8-C—N), 140.20 (t, 4-C$_{arom}$, $^2J_{C-F}$=22.6 Hz), 132.69 (q, 7-C$_{arom}$, $^2J_{C-F}$=33.7 Hz), 128.43 (s, 8-C$_{arom}$), 126.15 (s, C5-C—C4), 125.08 (s, 5-C$_{arom}$), 124.85 (s, 6-C$_{arom}$), 123.54 (q, 7-CCF$_3$, $^1J_{C-F}$=272.4 Hz), 116.20 (t, 3-C$_{arom}$, $^3J_{C-F}$=7.6 Hz), 114.02 (t, 2-CCHF$_2$, $^1J_{C-F}$=242.3 Hz), 112.98 (t, 4-CCHF$_2$, $^1J_{C-F}$=241.5 Hz) ppm.

C$_{12}$H$_6$F$_7$N (297): calcd (%) N, 4.71; C, 48.50; H, 2.04; found N, 4.74; C, 48.35; H, 2.10.

MP: 39.7-40° C.

EXAMPLE 64

2,4-Bis(difluoromethyl)-6-(trifluoromethyl)quinoline (I-29)

1,1,2,2-Tetrafluoro-N,N-dimethylethan-1-amine (TFEDMA) was activated by adding boron trifluoride diethyl etherate (1.2 eq., 236 mg, 0.211 mL, 1.66 mmol) in a solution of TFEDMA (1.2 eq., 241 mg, 0.195 mL, 1.66 mmol) in dry acetonitrile (5 mL) and stirred for 15 min. Then a solution of N-(1,1-difluoropropan-2-ylidene)-4-(trifluoromethyl)aniline (II-31) (1 eq., 328 mg, 1.39 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-29) as a grey solid in 23% yield (93.9 mg).

$^1$H NMR (400 MHz, CDCl$_3$; Me$_4$Si) δ=8.46 (s, 5-CH$_{arom}$), 8.37 (d, 8-CH$_{arom}$, $^3J_{H-H}$=8.9 Hz), 8.04 (dd, 7-CH$_{arom}$, $^3J_{H-H}$=8.9, $^4J_{H-H}$=1.8 Hz), 8.00 (s, 3-CH$_{arom}$), 7.20 (t, 4-CCHF$_2$, $^2J_{H-F}$=54.0 Hz), 6.82 (t, 2-CCHF$_2$, $^2J_{H-F}$=54.9 Hz) ppm.

$^{19}$F NMR (376 MHz, CDCl$_3$; CFCl$_3$) δ=−62.70 (s, CF$_3$), −114.48 (d, 2-CHF$_2$, $^2J_{F-H}$=54.0 Hz), −114.98 (d, 4-CHF$_2$, $^2J_{F-H}$=54.9 Hz) ppm.

$^{13}$C NMR (101 MHz, CDCl$_3$; Me$_4$Si) δ=154.90 (t, 2-C$_{arom}$, $^2J_{C-F}$=27.4 Hz), 148.77 (s, C8-C—N), 141.09 (t, 4-C$_{arom}$, $^2J_{C-F}$=22.5 Hz), 132.14 (s, 8-C$_{arom}$), 131.11 (q, 6-C$_{arom}$, $^2J_{C-F}$=33.1 Hz), 126.76 (q, 7-C$_{arom}$, $^3J_{C-F}$=2.9 Hz), 123.95 (t, C5-C—C4, $^3J_{C-F}$=2.5 Hz), 123.65 (q, CF$_3$, $^1J_{C-F}$=272.9 Hz), 121.81 (s, 5-C$_{arom}$), 115.71 (tt, 3-C$_{arom}$, $^3J_{C-F}$=7.6, $^3J_{C-F}$=2.2 Hz), 113.94 (t, 2-CCHF$_2$, $^1J_{C-F}$=243.4 Hz), 112.93 (t, 4-CCHF$_2$, $^1J_{C-F}$=241.9 Hz) ppm.

C$_{12}$H$_6$F$_7$N (297): calcd (%) N, 4.71; C, 48.50; H, 2.04; found N, 4.78; C, 48.51; H, 2.17.

MP: 57.7-58.3° C.

EXAMPLE 65

2,4-Bis(difluoromethyl)-8-phenylquinoline (I-30)

1,1,2,2-Tetrafluoro-N,N-dimethylethan-1-amine (TFEDMA) was activated by adding boron trifluoride diethyl etherate (1.2 eq., 489 mg, 0.437 mL, 3.45 mmol) in a solution of TFEDMA (1.2 eq., 500 mg, 0.403 mL, 3.45 mmol) in dry acetonitrile (5 mL) and stirred for 15 min. Then a solution of N-(1,1-difluoropropan-2-ylidene)-2-phenylaniline (II-33) (1 eq., 704 mg, 2.87 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-30) as a colourless solid in 28% yield (248.9 mg).

$^1$H NMR (400 MHz, CDCl$_3$; Me$_4$Si) δ=8.16 (dd, 5-CH$_{arom}$, $^3J_{H-H}$=8.5, $^4J_{H-H}$1.5 Hz), 8.00 (s, 3-CH$_{arom}$), 7.92 (dd, 7-CH$_{arom}$, $^3J_{H-H}$=7.2, $^4J_{H-H}$=1.3 Hz), 7.85-7.77 (m, 6-CH$_{arom}$), 7.76-7.70 (m, 5'-CH$_{arom}$), 7.58-7.45 (m, 6'-CH$_{arom}$), 7.24 (t, 4-CCHF$_2$, $^2J_{H-F}$=54.3 Hz), 6.74 (t, 2-CCHF$_2$, $^2J_{H-F}$=55.1 Hz) ppm.

$^{19}$F NMR (376 MHz, CDCl$_3$; CFCl$_3$) δ=−113.70 (d, 2-CHF$_2$, $^2J_{F-H}$=55.1 Hz), −114.97 (d, 4-CHF$_2$, $^2J_{F-H}$=54.3 Hz) ppm.

$^{13}$C NMR (101 MHz, CDCl$_3$; Me$_4$Si) δ=152.18 (t, 2-C$_{arom}$, $^2J_{C-F}$=27.8 Hz), 145.30 (s, C8-C—N), 142.28 (s, 1'-C$_{arom}$), 140.04 (t, 4-C$_{arom}$, $^2J_{C-F}$=22.0 Hz), 138.65 (s, 8-C$_{arom}$), 131.61 (s, 7-C$_{arom}$), 131.02 (s, 3',5'-C$_{arom}$), 129.09 (s, 6-C$_{arom}$), 128.06 (s, 2',6'-C$_{arom}$), 127.84 (s, 4'-C$_{arom}$), 125.29 (s, C5-C—C4), 122.83 (s, 5-C$_{arom}$), 114.68 (t, 2-CCHF$_2$, $^1J_{C-F}$=240.9 Hz), 114.17 (t, 3-C$_{arom}$, $^3J_{C-F}$=8.0 Hz), 113.25 (t, 4-CCHF$_2$, $^1J_{C-F}$=242.4 Hz) ppm.

C$_1$H$_{11}$F$_4$N (305): calcd (%) N, 4.59; C, 66.89; H, 3.63; found N, 4.71; C, 66.99; H, 3.70.

MP: 58.6-59.5° C.

EXAMPLE 66

2,4-Bis(difluoromethyl)-8-(phenylsulfanyl)quinoline (I-31)

1,1,2,2-Tetrafluoro-N,N-dimethylethan-1-amine (TFEDMA) was activated by adding boron trifluoride diethyl etherate (1.2 eq., 307 mg, 0.274 mL, 2.16 mmol) in a solution of TFEDMA (1.2 eq., 313 mg, 0.253 mL, 2.16 mmol) in dry acetonitrile (5 mL) and stirred for 15 min. Then a solution of N-(1,1-difluoropropan-2-ylidene)-2-(phenylsulfanyl)aniline (II-34) (1 eq., 500 mg, 1.8 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-31) as a colourless solid in 52% yield (308.7 mg).

$^1$H NMR (400 MHz, CDCl$_3$; Me$_4$Si) δ=7.99 (s, 3-CH$_{arom}$), 7.82 (d, 5-CH$_{arom}$, $^3J_{H-H}$=8.4 Hz), 7.66 (dd, 2',6'-CH$_{arom}$, $^3J_{H-H}$=6.4, $^4J_{H-H}$=3.0 Hz), 7.53-7.49 (m, 3',4', 5'-CH$_{arom}$), 7.47 (t, 6-CH$_{arom}$, $^3J_{H-H}$=8.0 Hz), 7.17 (t, 4-CCHF$_2$, $^2J_{H-F}$=54.3 Hz), 7.06 (d, 7-CH$_{arom}$, $^3J_{H-H}$=7.6 Hz), 6.89 (t, 2-CCHF$_2$, $^2J_{H-F}$=54.9 Hz) ppm.

$^{19}$F NMR (376 MHz, CDCl$_3$; CFCl$_3$) δ=−113.66 (d, 2-CHF$_2$, $^2J_{F-H}$=55.0 Hz), −115.22 (d, 4-CHF$_2$, $^2J_{F-H}$=.2 Hz) ppm.

$^{13}$C NMR (101 MHz, CDCl$_3$; Me$_4$Si) δ=151.47 (t, 2-C$_{arom}$, $^2J_{C-F}$=27.7 Hz), 143.85 (s, C8-C—N), 143.02 (s, 8-C$_{arom}$), 140.20 (t, 4-C$_{arom}$, $^2J_{C-F}$=22.2 Hz), 136.16 (s, 2',6'-C$_{arom}$), 130.89 (s, 1'-C$_{arom}$), 130.11 (s, 3',5'-C$_{arom}$), 129.64 (s, 4'-C$_{arom}$), 129.33 (s, 6-C$_{arom}$), 126.16 (s, 7-C$_{arom}$), 125.13 (s, C5-C—C4), 119.37 (s, 5-C$_{arom}$), 114.86 (t, 3-C$_{arom}$, $^3J_{C-F}$=7.9 Hz), 114.31 (t, 2-CCHF$_2$, $^1J_{C-F}$=242.4 Hz), 112.87 (t, 4-CCHF$_2$, $^1J_{C-F}$=241.4 Hz).

C$_{17}$H$_{11}$F$_4$NS (337): calcd (%) N, 4.15; C, 60.53; H, 3.29; found N, 4.22; C, 60.60; H, 3.36.

MP: 109.9-110.7° C.

EXAMPLE 67

2,4-Bis(difluoromethyl)benzo[h]quinolin-7-ol (I-32)

1,1,2,2-Tetrafluoro-N,N-dimethylethan-1-amine (TFEDMA) was activated by adding boron trifluoride diethyl etherate (1.2 eq., 362 mg, 0.323 mL, 2.55 mmol) in a solution of TFEDMA (1.2 eq., 370 mg, 0.298 mL, 2.55 mmol) in dry acetonitrile (5 mL) and stirred for 15 min. Then a solution of 5-[(1,1-difluoropropan-2-ylidene)amino]-1-naphthol (II-35) (1 eq., 500 mg, 2.13 mmol) in dry acetonitrile (5mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-20%) to provide the final compound (I-32) as a brown solid in 51% yield (321.7 mg).

$^1$H NMR (400 MHz, CDCl$_3$; Me$_4$Si) δ=8.90 (d, 10-CH$_{arom}$, $^3J_{H-H}$=8.3 Hz), 8.39 (d, 5-CH$_{arom}$, $^3J_{H-H}$=9.4 Hz), 8.04 (s, 3-CH$_{arom}$), 7.93 (d, 6-CH$_{arom}$, $^3J_{H-H}$=9.4 Hz), 7.61 (t, 9-CH$_{arom}$, $^3J_{H-H}$=8.0 Hz), 7.25 (t, 4-CCHF$_2$, $^2J_{H-F}$=54.4 Hz), 7.11 (d, 8-CH$_{arom}$, $^3J_{H-H}$=7.6 Hz), 6.92 (t, 2-CCHF$_2$, $^2J_{H-F}$=55.3 Hz), 5.43 (s, OH) ppm.

$^{19}$F NMR (376 MHz, CDCl$_3$; CFCl$_3$) δ=−113.93 (d, 2-CHF$_2$, $^2J_{F-H}$=55.3 Hz), −114.96 (d, 4-CHF$_2$, $^2J_{F-H}$=54.4 Hz) ppm.

$^{13}$C NMR (101 MHz, CDCl$_3$; Me$_4$Si) δ=151.71 (s, 7-C$_{arom}$), 151.27 (t, 2-C$_{arom}$, $^2J_{C-F}$=27.2 Hz), 146.29 (s, C10C—C—N), 139.47 (t, 4-C$_{arom}$, $^2J_{C-F}$=22.2 Hz), 132.81 (s, C5-C—C4+C10-C—CN), 128.23 (s, 9-C$_{arom}$), 124.51 (s, 5-C$_{arom}$), 123.57 (s, C7-C—C6), 118.94 (s, 6-C$_{arom}$), 117.77 (s, 10-C$_{arom}$), 114.73 (tt, 3-C$_{arom}$, $^3J_{C-F}$=7.6, $^3J_{C-F}$=2.2 Hz), 114.60 (t, 2-CCHF$_2$, $^1J_{C-F}$=241.0 Hz), 113.24 (s, 5-C$_{arom}$), 113.06 (t, 4-CCHF$_2$, $^1J_{C-F}$=242.4 Hz) ppm.

C$_{15}$H$_9$F$_4$NO (295): calcd (%) N, 4.74; C, 61.02; H, 3.07; found N, 4.82; C, 60.87; H, 3.14.

MP: 139.5-141.2° C.

EXAMPLE 68

4-[Chloro(fluoro)methyl]-2-(trifluoromethyl)quinoline (I-33)

N,N-Diethyl-2-chloro-1,1,2-trifluoroethylamine (Yarovenko's reagent) was activated by adding boron trifluoride diethyl etherate (1.2 eq., 454 mg, 0.41 mL, 3.21 mmol) in a solution of Yarovenko's reagent (1.2 eq., 868 mg, 0.73 mL, 3.21 mmol) in dry acetonitrile (5 mL) and stirred for 15 min. Then a solution of N-(1,1,1-trifluoropropan-2-ylidene)aniline (II-1) (1 eq., 500 mg, 2.67 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-33) as a light yellow solid in 57% yield (402 mg).

$^1$H NMR (400 MHz, CDCl$_3$; Me$_4$Si) δ=8.32 (d, 8-CH$_{arom}$, $^3J_{H-H}$=8.4 Hz), 8.13 (d, 5-CH$_{arom}$, $^3J_{H-H}$=8.5 Hz), 7.95 (s, 3-CH$_{arom}$), 7.92-7.88 (m, 7-CH$_{arom}$), 7.81-7.77 (m, 6-CH$_{arom}$), 7.66 (d, 4-CHFCl, $^2J_{H-F}$=48.9 Hz) ppm.

$^{19}$F NMR (376 MHz, CDCl$_3$; CFCl$_3$) δ=−67.65 (s, CF$_3$), −138.75 (d, 4-CHFCl, $^2J_{F-H}$=48.9 Hz) ppm.

$^{13}$C NMR (101 MHz, CDCl$_3$; Me$_4$Si) δ=148.02 (q, 2-C$_{arom}$, $^2J_{C-F}$=35.4 Hz), 147.88 (s, C8-C—N), 143.82 (d, 4-C$_{arom}$, $^2J_{C-F}$=21.1 Hz), 131.40 (s, 7-C$_{arom}$), 131.31 (s, 8-C$_{arom}$), 129.82 (s, 6-C$_{arom}$), 124.03 (d, C5-C—C4, $^2J_{C-F}$=3.6 Hz), 123.08 (s, 5-C$_{arom}$), 121.34 (q, 2-CCF$_3$, $^1J_{C-F}$=275.4 Hz), 113.04 (dq, 3-C$_{arom}$, $^3J_{C-F}$=9.9, $^3J_{C-F}$=2.0 Hz,), 96.75 (d, 4-CCHFCl, $^1J_{C-F}$=244.6 Hz) ppm.

C$_{11}$H$_6$F$_4$NCl (263): calcd (%) N, 5.31; C, 50.07; H, 2.27; found N, 5.11; C, 50.19; H, 2.65.

HRMS (ESI positive) for C$_{11}$H$_7$F$_4$NCl [M+H]: calcd 264.0198; found 264.0231.

MP: 49.4-50.4° C.

EXAMPLE 69

4-[Chloro(fluoro)methyl]-2-(difluoromethyl)quinoline (I-34)

N,N-Diethyl-2-chloro-1,1,2-trifluoroethylamine (Yarovenko's reagent) was activated by adding boron trifluoride diethyl etherate (1.2 eq., 503.8 mg, 0.45 mL, 3.55 mmol) in a solution of Yarovenko's reagent (1.2 eq., 673 mg, 0.56 mL, 3.55 mmol) in dry acetonitrile (5 mL) and stirred for 15 min. Then a solution of N-(1,1-difluoropropan-2-ylidene)aniline (II-14) (1 eq., 500 mg, 2.96 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-34) as a brown solid in 78 % yield (567 mg).

$^1$H NMR (400 MHz, CDCl$_3$; Me$_4$Si) δ=8.02 (d, 8-CH$_{arom}$, $^3J_{H-H}$=8.5 Hz), 7.88 (d, 5-CH$_{arom}$, $^3J_{H-H}$=8.5 Hz), 7.75 (s, 3-CH$_{arom}$), 7.62 (t, 7-CH$_{arom}$, $^3J_{H-H}$=7.7 Hz), 7.51-7.42 (m, 7-CH$_{arom}$+4-CCHFCl), 6.65 (t, 2-CCHF$_2$, $^2J_{H-F}$=55.1 Hz) ppm.

$^{19}$F NMR (376 MHz, CDCl$_3$; CFCl$_3$) δ=−114.5 (dd, 2-CHF$_2$, $^2J_{F-H}$=55.2 Hz, $^4J_{F-H}$=3 Hz), −138.0 (d, 4-CHFCl, $^2J_{F-H}$=49 Hz) ppm.

$^{13}$C NMR (101 MHz, CDCl$_3$; Me$_4$Si) δ=152.63 (t, 2-C$_{arom}$, $^2J_{C-F}$=27 Hz), 147.69 (s, C8-C—N), 143.25 (d, 4-C$_{arom}$, $^2J_{C-F}$=21 Hz), 130.80 (s, 7-C$_{arom}$), 130.70 (s, 8-C$_{arom}$), 128.96 (s, 6-C$_{arom}$), 123.68 (d, C5-C—C4, $^3J_{C-F}$=3.6 Hz), 123.06 (s, 5-C$_{arom}$), 114.33 (t, 2-CCHF$_2$, $^1J_{C-F}$=241.3 Hz), 113.0 (dt, 3-C$_{arom}$, $^3J_{C-F}$=9.6, $^3J_{C-F}$=1.9 Hz), 97.08 (d, 4-CCHFCl, $^1J_{C-F}$=244.3 Hz) ppm.

HRMS (ESI positive) for C$_{11}$H$_8$F$_3$NCl [M+H]: calcd 246.0292; found 246.0312.

EXAMPLE 70

4-[Chloro(fluoro)methyl]-6-fluoro-2-(trifluoromethyl)quinoline (I-35)

N,N-Diethyl-2-chloro-1,1,2-trifluoroethylamine (Yarovenko's reagent) was activated by adding boron trifluoride diethyl etherate (1.2 eq., 420 mg, 0.376 mL, 2.97 mmol) in a solution of Yarovenko's reagent (1.2 eq., 803 mg, 0.675 mL, 2.97 mmol) in dry acetonitrile (5 mL) and stirred for 15 min. Then a solution of 4-fluoro-N-(1,1,1-trifluoropropan-2-ylidene)aniline (II-7) (1 eq., 507 mg, 2.47 mmol) in dry acetonitrile (5 mL) was slowly added to this mixture via syringe. After 15 min at room temperature, the mixture was heated at 50° C. for 19 h. Acetonitrile was removed under reduced pressure. The title compound (I-35) was obtained after purification using ethyl acetate in pentane (0-5%) in mixture with the non-cyclised compound, the 1-chloro-1,5,5,5-tetrafluoro-4-((4-fluorophenyl)amino) pent-3-en-2-one with a ratio of 7:1.

Yield: 35% (by $^{19}$F NMR).

$^1$H NMR (400 MHz, CDCl$_3$; Me$_4$Si) δ=8.32 (dd, 8-CH$_{arom}$, $^3J_{H-H}$=9.3, $^4J_{H-F}$=5.5 Hz), 7.94 (s, 3-CH$_{arom}$), 7.75 (dd, 5-CH$_{arom}$, $^3J_{H-F}$=9.4, $^4J_{H-H}$=2.7 Hz), 7.65 (ddd, 7-CH$_{arom}$, $^3J_{H\text{-}F}$=9.4, $^4J_{H\text{-}F}$=7.9, $^4J_{H\text{-}H}$=2.7 Hz), 7.54 (d, 4-CCHFCl, $^2J_{H\text{-}F}$=48.7 Hz) ppm.

EXAMPLE 71

4-[Chloro(fluoro)methyl]-2-(difluoromethyl)-6-fluoroquinoline (I-36)

N,N-Diethyl-2-chloro-1,1,2-trifluoroethylamine (Yarovenko's reagent) was activated by adding boron trifluoride diethyl etherate (1.2 eq., 372 mg, 0.332 mL, 2.62 mmol) in a solution of Yarovenko's reagent (1.2 eq., 710 mg, 0.597 mL, 2.62 mmol) in dry acetonitrile (5 mL) and stirred for 15 min. Then a solution of N-(1,1-difluoropropan-2-ylidene)-4-fluoroaniline (II-20) (1 eq., 409 mg, 2.19 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-36) as a brown liquid in 3% yield (17 mg).

$^1$H NMR (400 MHz, CDCl$_3$; Me$_4$Si) δ=8.26 (dd, 8-CH$_{arom}$, $^3J_{H\text{-}H}$=9.3, $^4J_{H\text{-}F}$=5.5 Hz), 7.94 (s, 3-CH$_{arom}$), 7.77 (dd, 5-CH$_{arom}$, $^3J_{H\text{-}F}$=9.6, $^4J_{H\text{-}H}$=2.7 Hz), 7.63 (ddd, 7-CH$_{arom}$, $^3J_{H\text{-}H}$=9.3, $^4J_{H\text{-}F}$=8.0, $^4J_{H\text{-}H}$=2.7 Hz), 7.53 (d, 4-CCHFCl, $^2J_{H\text{-}F}$=48.9 Hz), 6.80 (t, 2-CCHF$_2$, $^2J_{H\text{-}F}$=55.0 Hz) ppm.

$^{19}$F NMR (376 MHz, CDCl$_3$; CFCl$_3$) δ=−106.78−−106.84 (m, F), −114.49 (dd, 2-CHF$_2$, $^2J_{F\text{-}H}$=55.0, $^4J_{F\text{-}H}$=2.9 Hz), −137.65 (d, 4-CHFCl, $^2J_{F\text{-}H}$=48.7 Hz) ppm.

$^{13}$C NMR (101 MHz, CDCl$_3$; Me$_4$Si) δ=161.61 (d, 6-C$_{arom}$, $^1J_{C\text{-}F}$=253.2 Hz), 152.11 (t, 2-C$_{arom}$, $^2J_{C\text{-}F}$=27.1 Hz), 144.94 (s, C8-C—N), 143.01 (dd, 4-C$_{arom}$, $^2J_{C\text{-}F}$=20.9, $^4J_{C\text{-}F}$=6.2 Hz), 133.56 (d, 8-C$_{arom}$, $^3J_{C\text{-}F}$=9.7 Hz), 128.42 (s, C5-C—C4), 121.43 (d, 7-C$_{arom}$, $^2J_{C\text{-}F}$=25.8 Hz), 114.11 (t, 2-CCHF$_2$, $^1J_{C\text{-}F}$=241.0 Hz), 114.10 (d, 3-C$_{arom}$, $^3J_{C\text{-}F}$=8.8 Hz), 107.65 (d, 5-C$_{arom}$, $^2J_{C\text{-}F}$=24.1 Hz), 97.09 (d, 4-CCHF$_2$, $^1J_{C\text{-}F}$=244.8 Hz) ppm.

HRMS (ESI positive) for C$_{11}$H$_7$F$_4$NCl [M+H]: calcd 264.0198; found 264.0198.

EXAMPLE 72

4-(1,2,2,2-Tetrafluoroethyl)-2-(trifluoromethyl)quinoline (I-37)

N,N-Diethyl-1,1,2,3,3,3-hexafluoropropylamine (Ishikawa's reagent) was activated by adding boron trifluoride diethyl etherate (1.2 eq., 462 mg, 0.41 mL, 3.26 mmol) in a solution of Ishikawa's reagent (1.2 eq., 1172 mg, 0.95 mL, 3.26 mmol) in dry acetonitrile (5 mL) and stirred for 15 min. Then a solution of N-(1,1,1-trifluoropropan-2-ylidene)aniline (II-1) (1 eq., 508 mg, 2.71 mmol) in dry acetonitrile (5 mL) was slowly added to this mixture via syringe. After 15 min at room temperature, the mixture was heated at 50° C. for 19 h. Acetonitrile was removed under reduced pressure and the reaction mixture was purified by flash chromatography using a gradient of ethyl acetate in pentane (0-5%) to provide the final compound (I-37) as a light brown solid in 14% yield (112 mg).

$^1$H NMR (400 MHz, CDCl$_3$; Me$_4$Si) δ=8.32 (d, 8-CH$_{arom}$, $^3J_{H\text{-}H}$=8.4 Hz), 7.99-7.97 (m, 5-CH$_{arom}$+3-CH$_{arom}$), 7.89 (t, 7-CH$_{arom}$, $^3J_{H\text{-}H}$=8.4 Hz), 7.78 (t, 6-CH$_{arom}$, $^3J_{H\text{-}H}$=8.3 Hz), 6.46 (dq, 4-CHFCF$_3$, $^2J_{H\text{-}F}$=43.9, $^3J_{H\text{-}F}$=5.5 Hz) ppm.

$^{19}$F NMR (376 MHz, CDCl$_3$; CFCl$_3$) δ=−67.72 (s, 2-CF$_3$), −77.25 (dd, 4-CHFCF$_3$, $^3J_{F\text{-}F}$=13.1, $^3J_{F\text{-}H}$=5.8 Hz), −198.87 (dq, 4-CHFCF$_3$, $^2J_{F\text{-}H}$=44.3, $^3J_{F\text{-}F}$=12.8 Hz) ppm.

$^{13}$C NMR (101 MHz, CDCl$_3$; Me$_4$Si) δ=147.72 (q, 2-C$_{arom}$, $^2J_{C\text{-}F}$=35.4 Hz), 147.51 (s, C8-C—N), 137.94 (d, 4-C$_{arom}$, $^2J_{C\text{-}F}$=19.1 Hz), 131.34 (s, 7-C$_{arom}$), 131.16 (s, 8-C$_{arom}$), 130.06 (s, 6-C$_{arom}$), 125.89 (d, C5-C—C4, $^2J_{C\text{-}F}$=3.7 Hz), 122.72 (s, 5-C$_{arom}$), 121.91 (q, 4-CHFCF$_3$, $^1J_{C\text{-}F}$=282.6 Hz), 121.68 (q, 2-CCF$_3$, $^1J_{C\text{-}F}$=282.6 Hz), 115.77 (d, 3-C$_{arom}$, $^3J_{C\text{-}F}$=10.4 Hz), 85.41 (dq, 4-CCHFCF$_3$, $^1J_{C\text{-}F}$=189.9, $^2J_{C\text{-}F}$=36.1 Hz) ppm.

C$_{12}$H$_6$F$_7$N (297): calcd (%) N 4.71; C 48.45; H 2.02; found N 4.71; C 48.80; H 2.32.

HRMS (ESI positive) for C$_{11}$H$_7$F$_7$N [M+H]: calcd 298.0461; found 298.0462.

MP: 58-58.8° C.

EXAMPLE 73

6-Fluoro-4-(1,2,2,2-tetrafluoroethyl)-2-(trifluoromethyl)quinoline (I-38)

N,N-Diethyl-1,1,2,3,3,3-hexafluoropropylamine (Ishikawa's reagent) was activated by adding boron trifluoride diethyl etherate (1.21 eq., 416 mg, 0.372 mL, 2.93 mmol) in a solution of Ishikawa's reagent (1.2 eq., 1050 mg, 0.854 mL, 2.92 mmol) in dry acetonitrile (5 mL) and stirred for 15 min. Then a solution of 4-fluoro-N-(1,1,1-trifluoropropan-2-ylidene)aniline (II-7) (1 eq., 498 mg, 2.43 mmol) in dry acetonitrile (5 mL) was slowly added to this mixture via syringe. After 15 min at room temperature, the mixture was heated at 50° C. for 19 h. Acetonitrile was removed under reduced pressure. The title compound (I-38) was obtained after purification using ethyl acetate in pentane (0 to 5%) in mixture with the non-cyclized compound, the 1,1,1,2,6,6,6-heptafluoro-5-((4-fluorophenyl)amino)hex-4-en-3-one with a ratio of 1:3. The yield was not determined; 64.7 mg of brown oil was obtained.

$^1$H NMR (400 MHz, CDCl$_3$; Me$_4$Si) δ=8.35 (dd, 8-CH$_{arom}$, $^3J_{H\text{-}H}$=9.3, $^4J_{H\text{-}F}$=5.5 Hz), 7.97 (s, 3-CH$_{arom}$), 7.72-7.65 (m, 5-CH$_{arom}$), 7.64-7.62 (m, 7-CH$_{arom}$), 6.33 (dq, 4-CHFCF$_3$, $^2J_{H\text{-}F}$=43.8, $^3J_{H\text{-}F}$=5.4 Hz) ppm.

HRMS (ESI positive) for C$_{12}$H$_6$F$_8$N [M+H]: calcd 316.0367; found 316.0375.

The invention claimed is:

1. Process for preparing a quinoline derivative of formula (I)

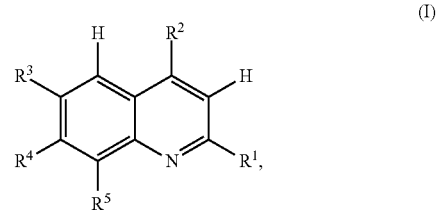

in which

R$^1$ is C$_{1\text{-}5}$-haloalkyl, aryl,

R$^2$ is C$_{1\text{-}5}$-haloalkyl, C$_{2\text{-}6}$-haloalkylhaloalkoxy and

R$^3$, R$^4$, R$^5$ are each independently selected from H, C$_{1\text{-}5}$-alkyl, halogen, C$_{1\text{-}5}$-haloalkoxy, C$_{1\text{-}6}$-alkoxy, aryl, C$_{1\text{-}4}$-dialkylamino, C$_{1\text{-}6}$-thioalkyl, thioaryl or R$_4$R$_5$ together form an annulated phenyl wherein one or more ketimines of formula (II)

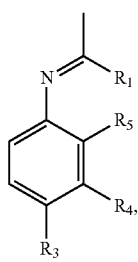

(II)

in which the radicals are as defined above,
are reacted with one or more fluoroalkylamino reagents of formula (III)

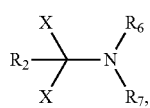

(III)

in which
X is F or Cl,
$R^6$ and $R^7$ are each independently selected from $C_{1-6}$-alkyl, $C_{3-8}$-cycloalkyl in the presence of Lewis Acid.

2. Process according to claim 1, wherein
$R^1$ is $CH_2F$, $CF_2H$, $CF_3$, $C_2F_5$,
$R^2$ is $CF_2H$, $CF_3$, CFHCl, $CF_3CFH$, $CFHOCF_3$,
$R^3$, $R^4$, $R^5$ are each independently selected from H, halogen, $CF_3O$, $N(CH_3)_2$, phenyl, $C_{1-6}$-thioalkyl, $C_{6-10}$-thioaryl, $C_{1-6}$-alkoxy, aryl, $C_{1-4}$-dialkylamino or $R_4R_5$ together form an annulated phenyl,
X is F,
$R^6$, $R^7$ are each independently selected from $CH_3$, $C_2H_5$.

3. Process according to claim 1, wherein
$R^1$ is $CF_2H$, $CF_3$,
$R^2$ is $CF_2H$, CFHCl, $CF_3CFH$, $R^3$ is H, F, $CF_3$, $CF_3O$, $N(CH_3)_2$,
$R^4$ is H, F, Cl, $OCH_3$, $OCF_3$, $N(CH_3)_2$, $CF_3$
or $R_4R_5$ together form an annulated phenyl,
$R^5$ is H, $OCH_3$, F, $OCF_3$, $CH_3$, phenyl, thiophenyl,
X is F,
$R^6$, $R^7$ are each independently selected from $CH_3$.

4. Process according to claim 1, in which the Lewis Acid is $BF_3$.

5. Process according to claim 1, in which one or more fluoroalkylamino reagents (III) are first reacted with $BF_3$ or $AlCl_3$ and then a compound of formula (II) is added in substance or dissolved in a solvent.

* * * * *